(12) United States Patent
Dosch et al.

(10) Patent No.: US 7,544,365 B2
(45) Date of Patent: Jun. 9, 2009

(54) TRPV1+ SENSORY NEURONS CONTROL OF β-CELLS STRESS AND ISLET INFLAMMATION IN DIABETES

(75) Inventors: Hans-Michael Dosch, Toronto (CA); Lan Tang, Toronto (CA); Yin Chan, Toronto (CA); Michael Salter, Etobicoke (CA)

(73) Assignee: The Hospital for Sick Children, Toronto (CA)

( * ) Notice: Subject to any disclaimer, the term of this patent is extended or adjusted under 35 U.S.C. 154(b) by 0 days.

(21) Appl. No.: 11/638,830

(22) Filed: Dec. 14, 2006

(65) Prior Publication Data

US 2008/0145386 A1    Jun. 19, 2008

(51) Int. Cl.
   *A61K 45/00* (2006.01)
   *A61K 39/00* (2006.01)
   *C07K 5/00* (2006.01)
   *C07K 14/00* (2006.01)

(52) U.S. Cl. ................. 424/278.1; 424/198.1; 530/300; 530/350; 514/866

(58) Field of Classification Search ....................... None
   See application file for complete search history.

(56) References Cited

U.S. PATENT DOCUMENTS

2007/0060512 A1* 3/2007 Sadeghi et al. ................. 514/12

FOREIGN PATENT DOCUMENTS

WO PCT/US2004/006462   * 3/2004

OTHER PUBLICATIONS

Santoni et al. Jour Neuroimmunol 68: 131-138, 1996.*
Sjogern et al. Jour Autoimmun 24: 269-279, 2005.*
Razavi et al. Cell 127: 1123-1135, 2006.*
Carlsson et al. Eur J Pharm 312: 75-81, 1996.*
Bour-Jordan and Bluestone, Cell 127: 1097-1099, 2006.*
Pietropaolo et al. Diabetes 56: 1189-1197, 2007.*
Ahren, et al. "Autonomic regulation of islet hormone secretion - implications for health and disease", *Diabetologia*, vol. 43: pp. 393-410 (2000).
Amrani et al., "Glucose homeostasis in the nonobese diabetic mouse at the prediabetic stage", *Endocrinology*, vol. 3: No. 3: pp. 1115-1124 (1998).
Amrani et al., "Progression of autoimmune diabetes driven by avidity maturation of a T-cell population", *Nature*, vol. 406: pp. 739-742 (2000).
Amrani et al., "Expansion of the antigenic repertoire of a single T cell receptor upon T cell activation", *The Journal of Immunology*, vol. 167: pp. 655-666 (2001).
Anderson et al., "Prevalent CD8+ T cell response against one peptide/MHC complex in autoimmune diabetes", *Proc. Natl. Acad. Sci. USA*. vol. 96: pp. 9311-9316 (1999).
Anderson et al., "The NOD mouse: a model of immune dysregulation", *Annu. Rev. Immunol.*, vol. 23: pp. 447-485 (2005).

Babaya et al. "Susceptibility to stretozotocin-induced diabetes is mapped to mouse chromosome 11", *Biochemical and Biophysical Research Communications*, vol. 328: pp. 158-164 (2005).
Barakat et al., "Calcitonin gene-related peptide and islet amyloid polypeptide stimulate insulin secretion in RINm5F cells through a common receptor coupled to a generation of cAMP", *Bioscience Reports*, vol. 14: No. 1: pp. 1-13 (1994).
Bluestone et al., "How do CD4+CD25+ regulatory T cells control autoimmunity?", *Current Opinion In Immunology*, vol. 17: pp. 638-642 (2005).
Bretherton-Watt et al., "The Physiology of calcitonin gene-related peptide in the islet compared with that of islet amyloid polypeptide (amylin)", *Annals New York Academy of Sciences*, pp. 299-312 (1992).
Butterfield et al., "New genetic loci that control susceptibility and symptoms of experimental allergic encephalomyelitis in inbred mice", *The Journal of Immunology*, vol. 161: pp. 1860-1867 (1998).
Butterfield et al., "Genetic analysis of disease subtypes and sexual dimorphisms in mouse experimental allergic encephalomyelitis (EAE): relapsing/remitting and monophasic remitting/nonrelapsing EAE are immunogenetically distinct", *The Journal of Immunology*, vol. 162: pp. 3096-3102 (1999.)
Carrillo et al., "Islet-infiltrating B-cells in nonobese diabetic mice predominantly target nervous system elements", *Diabetes*, vol. 54: pp. 69-77 (2005).
Caterina et al., "Impaired nociception and pain sensation in mice lacking the capsaicin receptor", *Science*, vol. 288: pp. 306-313 (2000).
Chancellor-Freeland et al., "Substance P and stress-induced changes in macrophages", *Annals New York Academy of Sciences*, pp. 472-484 (1995).
Chaparro et al., "Nonobese diabetic mice express aspects of both type 1 and type 2 diabetes", *PNAS*, vol. 103: No. 33: pp. 12475-12480 (2006).
Cua et al., "Macrophages regulate induction of delayed-type hypersensitivity and experimental allergic encephalomyelitis in SJL mice", *Eur. J. Immunol.*, vol. 25: pp. 2318-2324 (1995).
Freeman, et al., "Deletion of Nicotinamide Nucleotide Transhydrogenase - a new quantative trait locus accouting for glucose intolerance in C57BL/6J mice", *Diabetes*, vol. 55: pp. 2153-2156 (2006).

(Continued)

*Primary Examiner*—Jeffrey Stucker
*Assistant Examiner*—Aditi Dutt
(74) *Attorney, Agent, or Firm*—Jagtiani & Guttag

(57) ABSTRACT

A process is disclosed for controlling inflammatory tissue access through release of neuropeptides, such as substance P (sP), to insulin-responsive sensory neurons, whereby simultaneous control of insulin sensitivity/resistance is manifested. In models of Type 1 and Type 2 diabetes, sensory afferents, in particular TRPV1, have fundamental roles in insulin/glucose homeostasis, islet physiology and autoimmune tissue inflammation. By manipulation of the TRPV1 neuro-β-cell circuit or enhancement of pancreatic sP levels, normalization of insulin resistance, clearance of inflammation and prevention of both Type 1 and Type 2 diabetes is realized.

1 Claim, 19 Drawing Sheets
(9 of 19 Drawing Sheet(s) Filed in Color)

OTHER PUBLICATIONS

Grattan et al., "Congenic mapping of the diabetotgenic locus ldd4 to a 5.2-cM region of chromosome 11 in NOD mice", *Diabetes*, vol. 51: pp. 215-223 (2002).

Hadaya et al., "G-CSF treatment prevents cyclophosphamide acceleration of autoimmune diabetes in the NOD mouse", *Journal of Autoimmunity*, vol. 24: pp. 125-134 (2005).

Helme et al., "The effect of substance P on the regional lymph node antibody response to antigenic stimulation in capsaicin-pretreated rates", *Journal of Immunology*; vol. 139: No. 10: pp. 3470-3474 (1987).

Hermansen et al., "Dual effects of calcitonin gene-related peptide on insulin secretion in the prefused dog pancreas", *Regulatory Peptides*, vol. 27: pp. 149-157 (1990).

Indo et al, "Mutations in the TRKA/NGF receptor gene in patients with congenital insensitivity to pain with anhidrosis", *Nature Genetics*, vol. 13: pp. 485-488 (1996).

Ivakine et al., "Sex-specific effect of insulin-dependent daibetes 4 on regulation of diabetes pathogenesis in the nonobese diabetic mouse", *Journal of Immunology*, vol. 174: pp. 7129-7140 (2005).

Ji et al., "Different modes of pathogenesis in T-cell-dependent autoimmunity: clues from two TCR transgenic systems", *Immunological Reviews*, vol. 169: pp. 139-146 (1999).

Keymeulen et al., "Insulin needs after CD3-antibody therapy in new-onset type 1 diabetes", *The New England Journal of Medicine*, vol. 352: pp. 2598-2608 (2005).

Khachatryan et al., "Targeted expression of the neuropeptide calcitonin gene-related peptide to β cells prevent diabetes in NOD mice", *Journal of Immunology*, vol. 158: pp. 1409-1416 (1997).

LeRoith et al., "Mouse models created to study the pathophysiology of type 2 diabetes", *The International Journal of Biochemistry and Cell Biology*, vol. 38: pp. 904-912 (2006).

Lieberman et al., "Identification of the β cell antigen targeted by a prevalent population of pathogenic CD8+ T cells in autoimmune diabetes", *PNAS*, vol. 100: No. 14: pp. 8384-8388 (2003).

Mathis et al., "β-cell death during progression to diabetes", *Nature*, vol. 414: pp. 792-798 (2001).

McAleer et al., "Crosses of NOD mice with the related NON strain: a polygenic model for IDDM.(insulin-dependent diabetes mellitus)", *Diabetes*, vol. 44: pp. 1186-1196 (1995).

Moesgaard et al., "Sensory nerve inactivation by resiniferatoxin improves insulin sensitivity in male obese Zucker rats", *Am. J. Physical Endocrinol. Metab.*, vol. 288: pp. 1137-1145 (2005).

Morikawa et al., "The role of antigen-presenting cells in the regulation of delayed-type hypersensitivity", *Cellular Immunology*, vol. 152: pp. 200-210 (1993).

Nielsen et al., "Gene expression profiles during beta cell maturation and after IL-1β exposure reveal important roles of Pdx-1 and Nkx6.1 for IL-1β sensitivity", *Diabetologia*, vol. 48: pp. 2185-2199 (2004).

Nilsson et al., "Effects on immune responses in rats after neuromanipulation with capsaicin", *Int. J. Immunopharmac.*, vol. 13: No. 1: pp. 21-26 (1991).

O'Connor et al., "The role of substance P in inflammatory disease", *Journal of Cellular Physiology*, vol. 201: pp. 167-180 (2004).

Parekh et al., "Reversal of diet-induced obesity and diabetes in C57BL/6J mice", *Metabolism*, vol. 47: No. 9: pp. 1089-1096 (1998).

Persson-Sjogren et al., "Expression of the NK-1 receptor on islet cells and invading immune cells in the non-obese diabetic mouse", *Journal of Autoimmunity*, vol. 24: pp. 269-279 (2005).

Pop et al., "Single cell analysis shows decreasing FoxP3 and TGFβ1 coexpressing CD4+CD25+ regulatory T cells during autoimmune diabetes", *JEM*, vol. 201: No. 8: pp. 1333-1346 (2005).

Prescott et al., "A modular $PIP_2$ binding site as a determinant of capsaicin recptor sensitivity", *Science*, vol. 300: pp. 1284-1288 (2003).

Rosmalen et al., "Islet abnormalities associated with an early influx of dendritic cells and macrophages in NOD and NOD scid mice", *Laboratory Investigation*, vol. 80: No. 5: pp. 769-777 (2000).

Rosmalen et al., "Islet abnormalities in the pathogenesis of autoimmune diabetes", *TRENDS in Endoctrinology and Metabolism*, vol. 13: No. 5: pp. 209-214 (2002).

Salomon et al., "Development of Spontaneous autoimmune peripheral polyneuropathy in B7-2-deficient NOD mice", *J. Exp. Med.*, vol. 194: No. 5: 677-684 (2001).

Santoni et al., "Capsaicin-induced inhibition of mitogen and interleukin-2-stimulated T cell proliferation: its reversal by in vivo substance P administration", *Journal of Neuroimmunology*, vol. 68: pp. 131-138 (1996).

Sathianathan et al., "Insulin induces cobalt uptake in a subpopulation of rat cultured primary sensory neurons", *European Journal of Neuroscience*, vol. 18: pp. 2477-2486 (2003).

Serreze et al., "Use of recombinant congenic and congenic strains of NOD mice to identify a new insulin-dependent diabetes resistnace gene", *Journal of Experimental Medicine*, vol. 180: pp. 1553-1558 (1994).

Trudeau et al., "Neonatal β-cell apoptosis - A trigger for autoimmune diabetes?", *Diabetes*, vol. 49: pp. 1-7 (2000).

Van Buren et al., "Sensitization and translocation of TRPVI by insulin and IGF-I", *Molecular Pain*, vol. 1: pp. 1-11 (2005).

van de Wall et al., "Ablation of capsaicin-sensitive afferent nerves affects insulin response during an intravenous glucose tolerance test", *Life Sciences*, vol. 77: pp. 1238-1292 (2005).

Verdaguer et al., "Acceleration of spontaneous diabetes in TCR-β-transgenic nonobese diabetic mice by β-cell cytotoxin CD8+ T cells expressing identical TCR-α-chains", *Journal of Immunology*, vol. 157: pp. 4726-4735 (1996).

Verdaguer et al., "Spontaneous autoimmune diabetes in monoclonal T cell nonobese diabetic mice", *J. Exp. Med.*, vol. 186: No. 10: pp. 1663-1676 (1997).

Wang et al., "Nicotinic acethlcholine receptor α7 subunit is an essential regulator of inflammation", *Nature*, vol. 421: pp. 384-388 (2003).

Winer et al., "Type I diabetes and multiple sclerosis patients target islet plus central nervous system autoantigens; nonimmunized nonobese diabetic mice can develop autoimmune encephalitis", *Journal of Immunology*, vol. 166: pp. 2831-2841 (2001).

Winer et al., "Autoimmune islet destruction in spontaneous type 1 diabetes is not β-cell exclusive", *Nature Medicine*, vol. 9: No. 2 pp. 198-205 (2003).

Zhang et al., "I situ β cell death promotes priming of diabetogenic CD8 T lymphocytes", *Journal of immunology*, vol. 168: pp. 1466-1472 (2002).

DiLorenzo, et al. "Major histocompatibility complex class I-restricted T cells are required for all but the end stages of diabetes development in nonobese diabetic mice and use a prevalent T cell receptor α chain gene rearrangement", *Proc. Natl. Acad. Sci. USA*, vol. 95: pp. 12538-12543 (1998).

* cited by examiner

Systemic immune system:
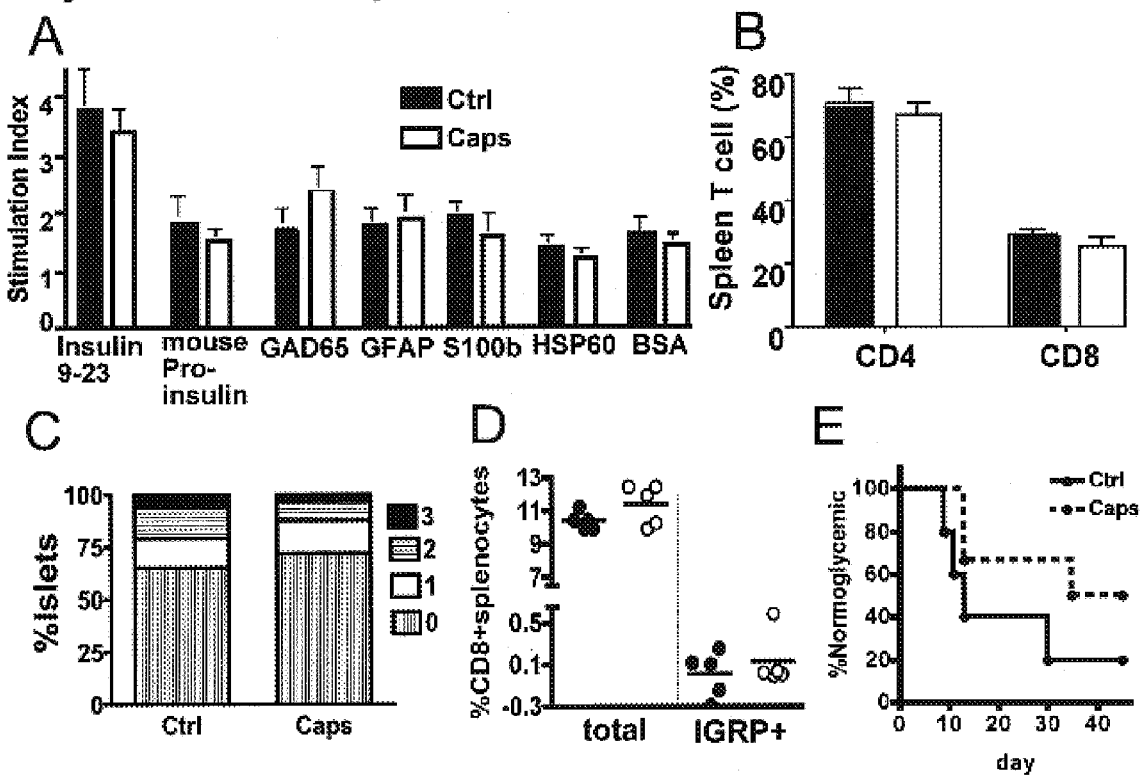
Pancreatic Lymph Node:
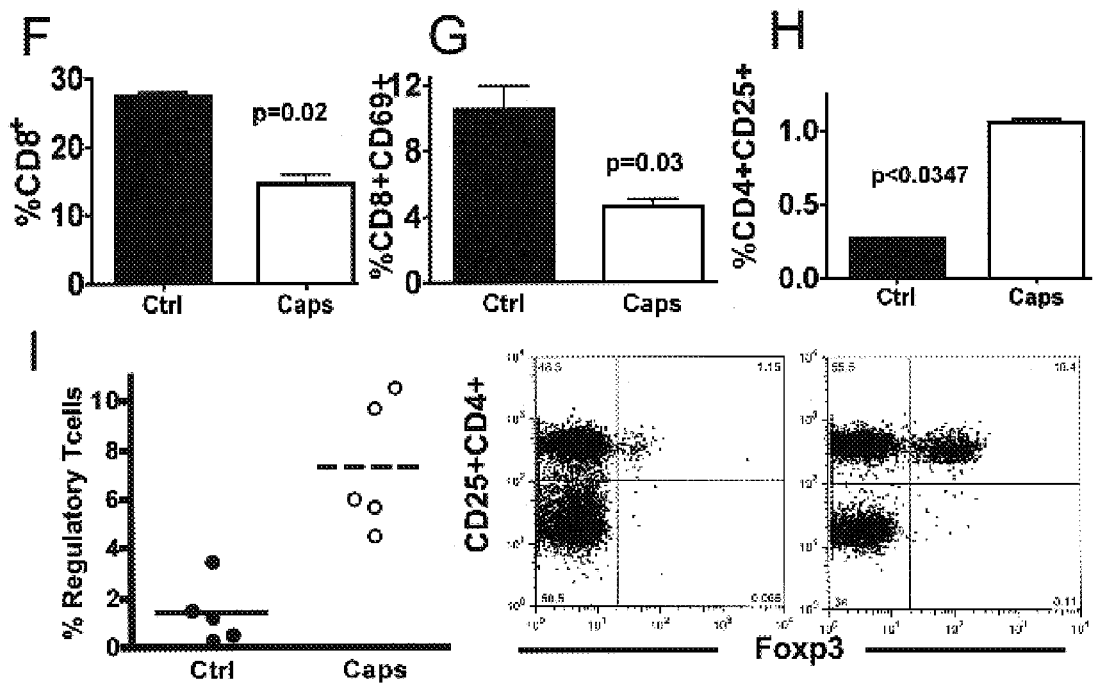
FIGURE 2A - 2I

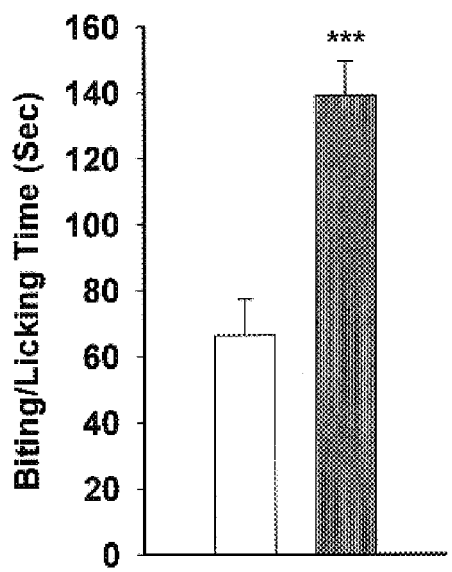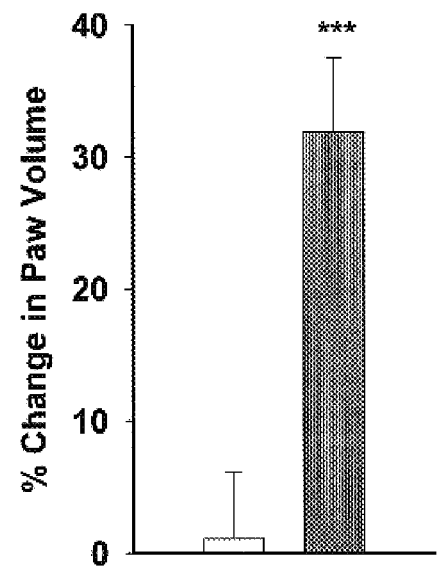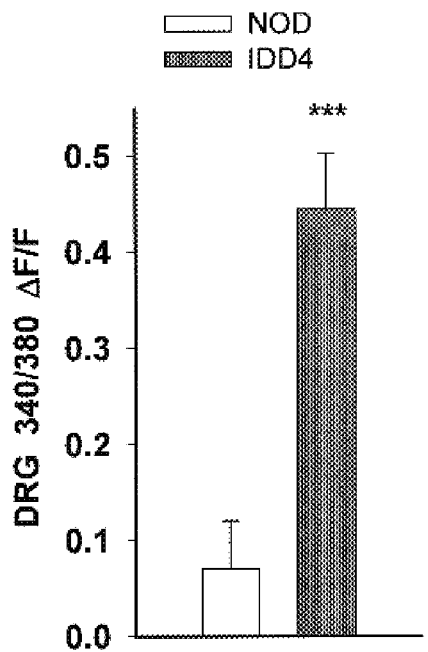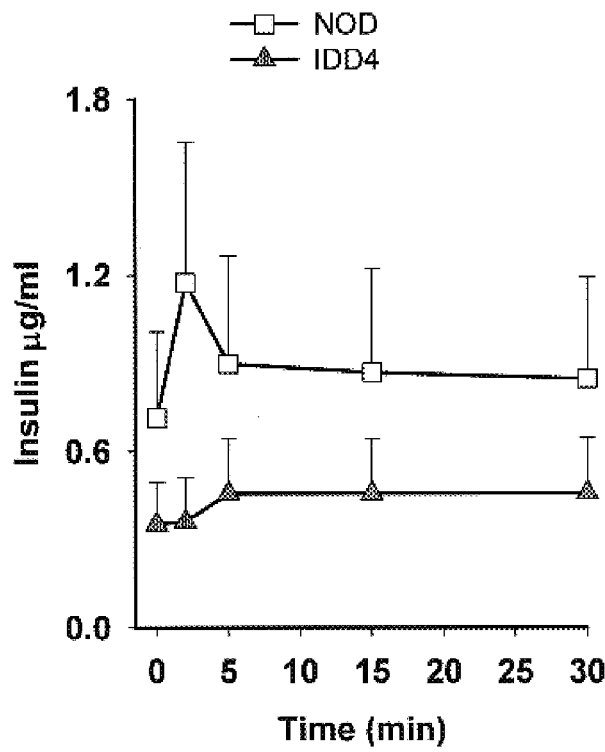

FIGURE 10
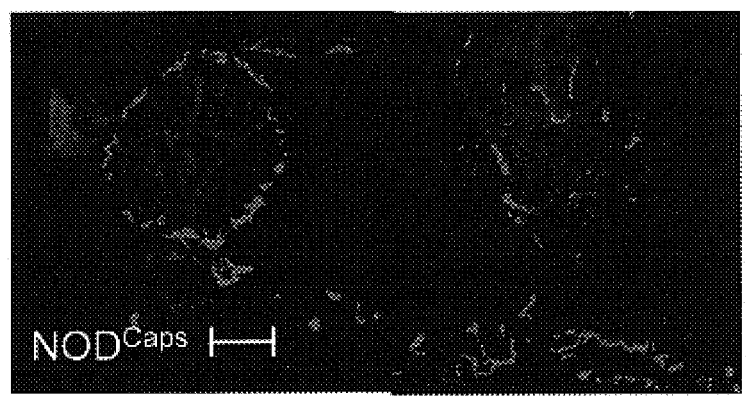
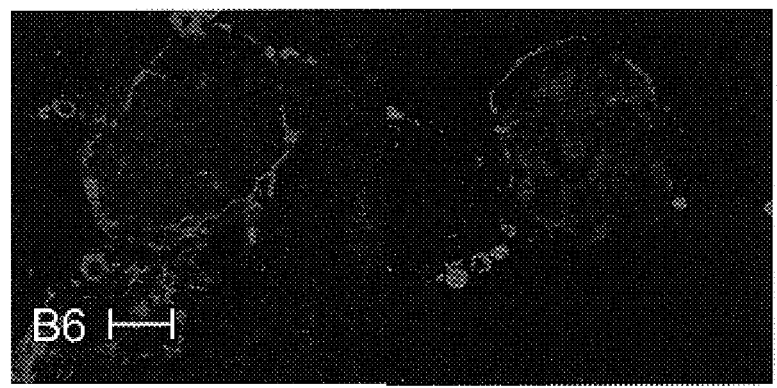
GFAP/ Insulin/ sP

FIGURE 11
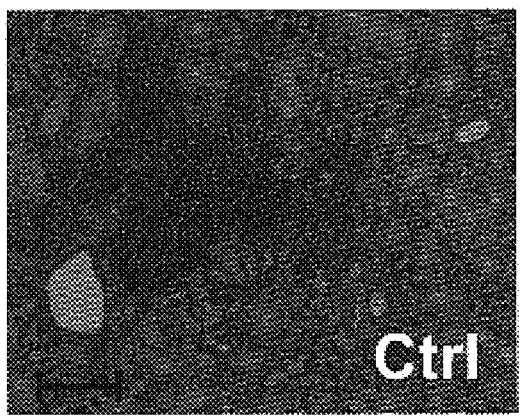 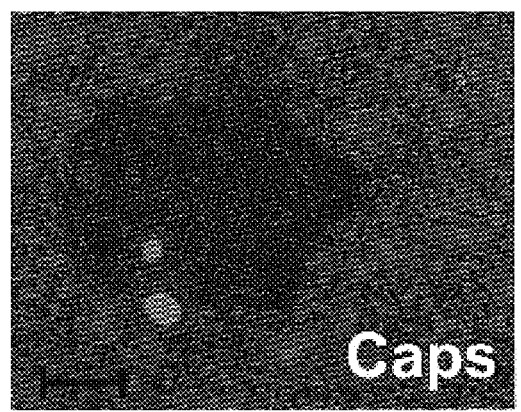

US 7,544,365 B2

TRPV1+ SENSORY NEURONS CONTROL OF β-CELLS STRESS AND ISLET INFLAMMATION IN DIABETES

FIELD OF THE INVENTION

This invention generally relates to nervous system involvement in the manifestation of insulitis and diabetes; particularly to the mechanisms of the transient receptor potential vanilloid-1 receptor (TRPV1), as such mechanism relates to clear chronic inflammatory cell infiltrations; and most particularly to the use of Substance P, or similar neuropeptides from sensory afferent neurons, as agents effective for the normalization of elevated insulin resistance and for the rapid resolution of tissue inflammation and infiltration by immune cells.

BACKGROUND OF THE INVENTION

Type 1 diabetes (T1D) is an autoimmune disease observed in many mammalian species, governed by multiple genetic and environmental risk factors. Overt diabetes reflects glucose intolerance due to insulin deficiency. It is the end result of prediabetes, with progressive lymphoid infiltration around and then inside pancreatic islets of Langerhans, and subsequent destruction of insulin-producing β-cells by autoreactive T lymphocytes (Anderson and Bluestone, 2005). T1D is characterized by a permissive immune system that fails to impose tolerance to arrays of self-antigens. Although the initiating events are not fully understood, β-cell stress and β-cell death in the course of early islet restructuring are thought to provide sensitizing autoantigens which expand autoreactive T cell pools in pancreatic lymph nodes (Mathis et al., 2001; Rosmalen et al., 2002; Trudeau et al., 2000; Zhang et al., 2002).

Self-antigens targeted in T1D are expressed in β-cells and, in most cases, elsewhere in the body. They prominently include neuronal antigens, recognized by T cells with pathogenic potential (Salomon et al., 2001; Winer et al., 2001). It is unclear why, in T1D, T cells infiltrate only islets and their associated glia (Winer et al., 2003). It is also unclear whether autoimmunity and islet inflammation are related to hyperinsulinism and insulin resistance typical for even young NOD mice (Amrani et al., 1998; Chaparro et al., 2006).

There is evidence for functional interactions between nervous and immune systems (e.g. (Wang et al., 2003)), but connections between islet autoimmunity and the nervous system remain ill defined (Carrillo et al., 2005). The interface between nervous system, external and tissue environments is the primary sensory afferent neuron. Primary afferents also have efferent function through local release of mediators such as neuropeptides (e.g. substance P, sP and CGRP). There is evidence that islets may be innervated by primary sensory neurons, but their local function is uncertain (Ahren, 2000).

SUMMARY OF THE INVENTION

With regard to Type I diabetes, it is known that T-cell-mediated death of pancreatic β-cells leads to insulin deficiency, although the mechanism behind what attracts and restricts broadly autoreactive lymphocyte pools to the pancreas remains unclear. The data disclosed herein point to a fundamental role for insulin-responsive TRPV1+ sensory neurons in β-cell function diabetes pathoetiology.

The instant inventors have now determined that in diabetes-prone NOD mice, the role of insulin-responsive TRPV1+ sensory neurons plays a role in the regulation of both islet autoimmunity and of β-cell stress from insulin resistance. The instant disclosure demonstrates that eliminating these neurons prevents islet inflammation and diabetes, whereas systemic, pathogenic T-cells autoreactivity persists. Additionally, it has been determined that the insulin resistance and β-cell stress of prediabetic NOD mice fail to develop when TRPV1+ neurons are eliminated. TRPV1$^{NOD}$ in the Idd4.1 T1D-risk locus, is a hypo-functional mutant, mediating depressed neurogenic inflammation.

It is herein demonstrated that delivering a mediator of neurogenic inflammation, substance P, by intra-arterial injection into the NOD pancreas rapidly reverses islet inflammation, abnormal insulin resistance and diabetes for several weeks in animals with sufficient β-cell reserve. Concordantly, TRPV1-knockout significantly enhances insulin-sensitivity, while insulitis/diabetes-resistant NOD×B6Idd4 congenic mice, carrying wild type TRPV1, show restored TRPV1 function and insulin sensitivity.

Accordingly, it is a primary objective of the instant invention to demonstrate the relationship between the presence of TRPV1+ sensory afferent neurons, and the manifestation of insulitis and diabetes.

It is a further objective of the instant invention to demonstrate that elimination of these neurons, in a selective manner, is effective to prevent islet inflammation and diabetes (both Type I and Type II), although systemic, pathogenic T-cell autoreactivity nevertheless persists.

It is yet another objective of the instant invention to demonstrate that appropriate delivery of a mediator of neurogenic inflammation, such as Substance P, is effective, at least transiently, to rapidly reverse islet inflammation, abnormal insulin resistance and Type I and Type II diabetes, in subjects with sufficient β-cell reserve.

It is a still further objective of the invention to demonstrate that an insufficiency in the release of Substance P results in manifestation of insulin resistance and the development of both Type I and Type II diabetes.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A-2E compare development and function of systemic T cells in NOD$^{caps}$ and NOD$^{ctrl}$ mice. FIG. 2A particularly shows that systemic T-cell pools autoreactive to islet, pSC and other disease associated antigens were indistinguishable in NOD$^{caps}$ and NOD$^{ctrl}$ spleen cells;

FIG. 2F-2I illustrate the comparative development and function of pancreatic T cells in NOD$^{caps}$ and NOD$^{ctrl}$ mice

FIGS. 8A-8D illustrate that TRPV1 plays a fundamental role in islet inflammation and insulin homeostasis, using NOD.B6.Idd4-congenic mice;

FIG. 10 illustrates that NOD$^{ctrl}$ and NOD.scid pancreas shows accumulation of more sP in nerve endings that B6 mice;

FIG. 11 illustrates Sjogren like sialitis in both NOD$^{ctrl}$ and NOD$^{caps}$ mice;

DETAILED DESCRIPTION OF THE INVENTION

It is known that a prominent subset of sensory neurons expresses the Transient Receptor Potential Vanilloid-1 (TRPV1) protein, a non-specific cation channel that was first identified as the receptor for capsaicin (Caterina et al., 2000; Prescott and Julius, 2003). It is further known that TRPV1+ neurons are of importance in proinflammatory reactions (O'Connor et al., 2004), and that islet infiltrating lymphocytes express receptors for neuropeptides (Persson-Sjogren et al., 2005). Thus, the instant inventors set out to investigate the possibility that these sensory neurons may have a role in T1D.

Figures 1A, 1B, 1C, 1D, 1E, 1F:
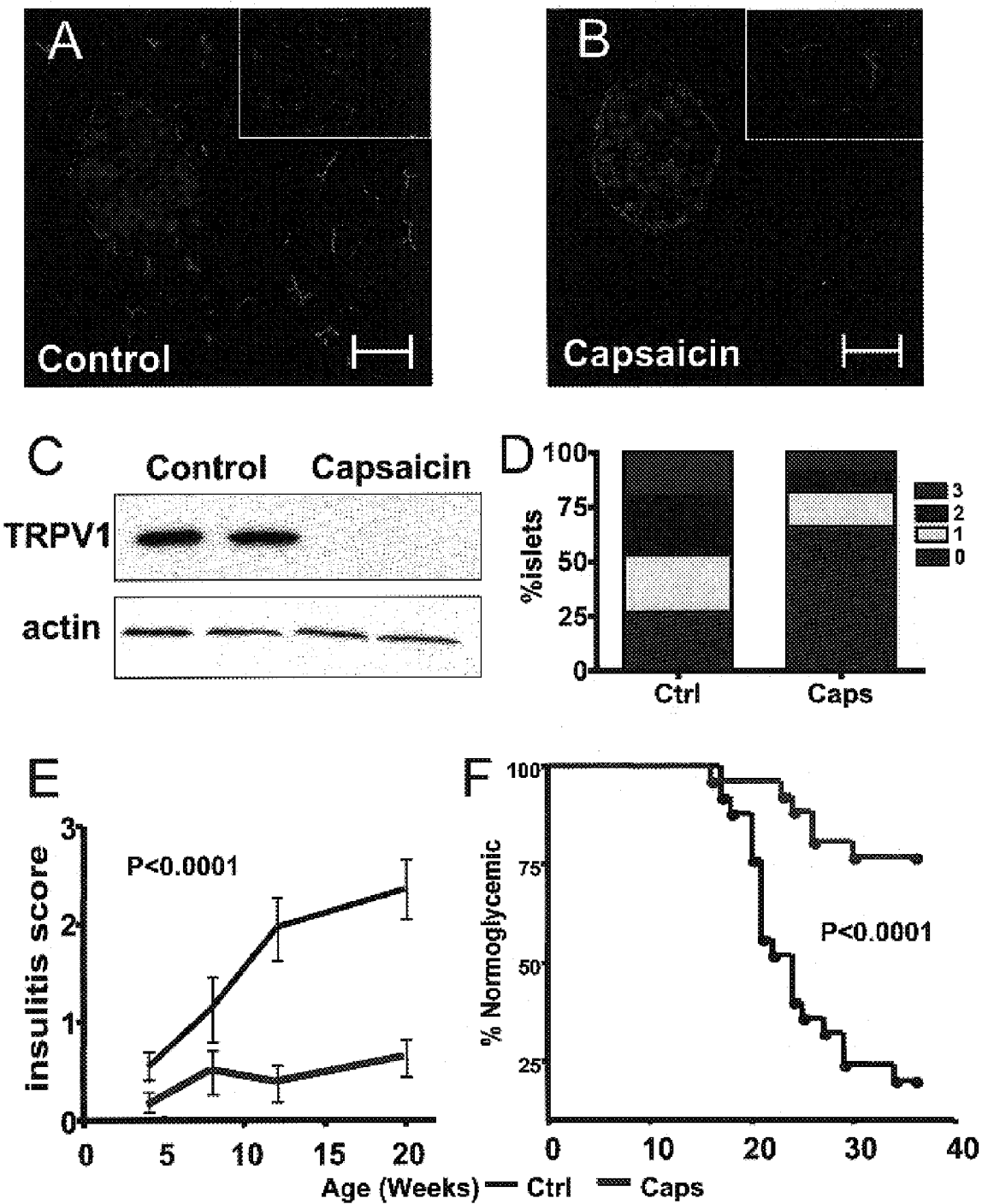
FIG. 1A illustrates, via immunofluorescence, the association of murine islets with meshworks of TRPV1+ fibers.
FIG. 1B illustrates that TRPV1 was undetectable in endocrine islet cells by immunofluorescence
FIG. 1C illustrates Western blots in randomly selected 5-6 week old control and diabetic animals.
FIG. 1D illustrates that in NOD$^{caps}$ mice, islet infiltrations were significantly reduced, compared with NOD$^{ctrl}$.
FIG. 1E illustrates that in NOD$^{caps}$ mice most islets remained free of lymphocytes, and there was little insulitis progression over time.
FIG. 1F illustrates that capsaicin treatment delayed the onset of diabetes and reduced its incidence.
Figure 9:
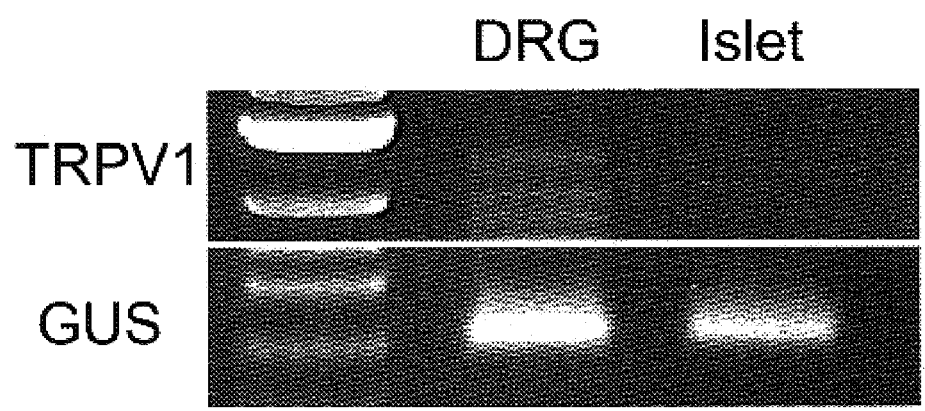
FIG. 9 illustrates that TRPV1 was undetectable in endocrine cells by RT-PCR of purified NOD islets.
Figure 12:
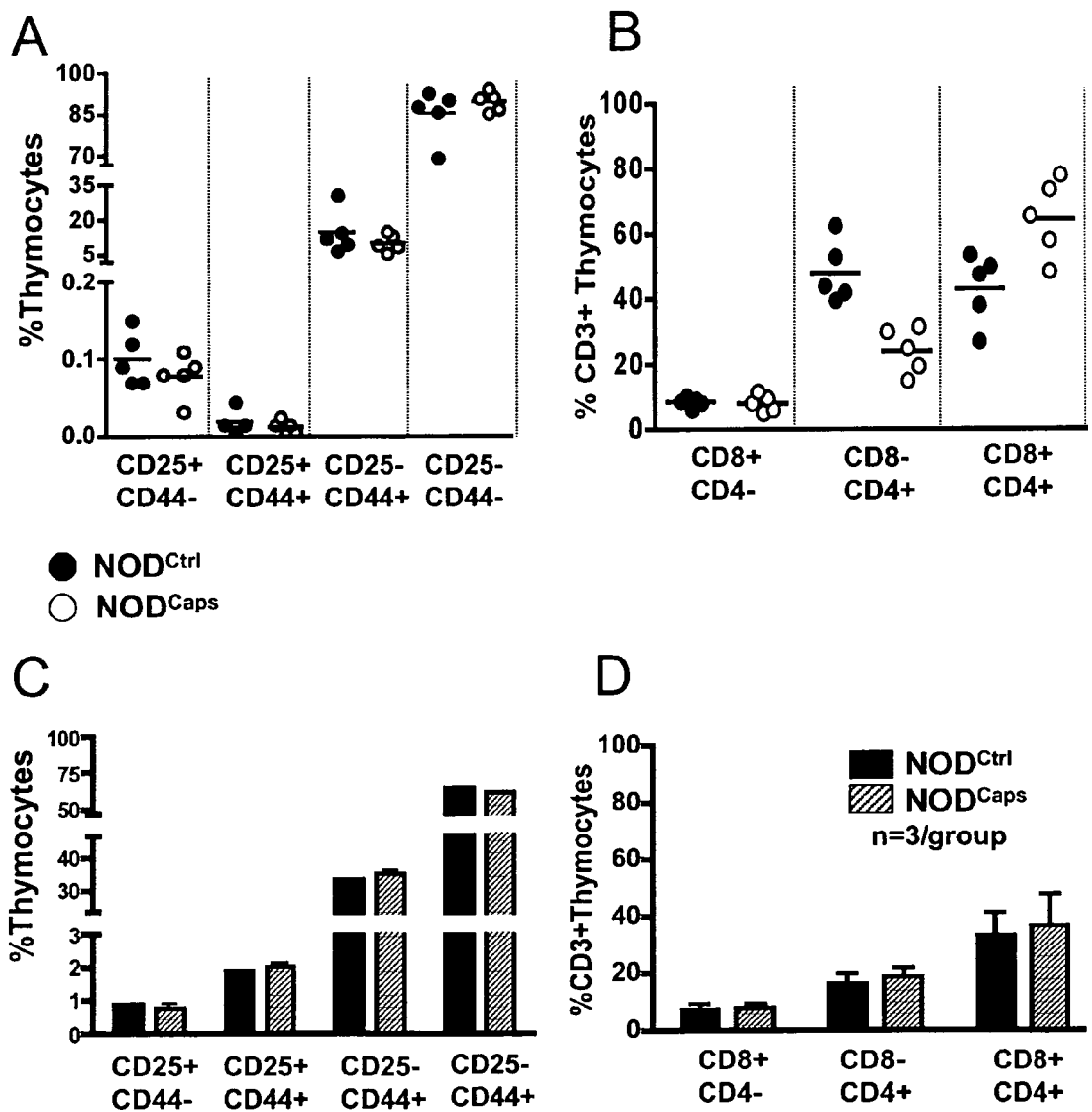
FIGS. 12A-12D illustrate NOD$^{ctrl}$ and NOD$^{caps}$ thymocyte subpopulations at 10 days and 6-8 weeks of age.

Results: TRPV1+ sensory afferents control onset of islet inflammation & diabetes Using immunofluorescence, it was observed that murine islets are associated with meshworks of TRPV1+ fibers (FIG. 1a). TRPV1 was undetectable in endocrine islet cells by immunofluorescence (FIG. 1a, b) and by RT-PCR of purified NOD islets (FIG. 9). based on this evidence of islet innervation by TRPV1+ primary afferent sensory neurons, we investigated their possible role in T1D pathogenesis, using neonatal treatment of diabetes-prone NOD mice with capsaicin to permanently remove these neurons (Caterina and Julius, 2001; Jancso et al., 1977). Two day-old NOD mice received capsaicin (50 mg/kg, s.c.) or vehicle (NOD$^{caps}$, NOD$^{ctrl}$). As expected from the voluminous literature, capsaicin-treated mice were viable, fertile, without abnormalities in growth or gross tissue structure, including pancreas. We confirmed the lack of TRPV1 expression in NOD$^{caps}$ mice, using immunofluorescence (FIG. 1a, b, TRPV1 green), Western blots (8, 12 & 20 wk), and standard hot-plate testing in randomly selected 5-6 wk old or in diabetic animals (FIG. 1c). Consistent with loss of neuropeptide secreting TRPV1+ neurons, NOD$^{caps}$ mice showed no sP staining (FIG. 10).

Islet infiltration by hematopoietic inflammatory cells begins by 4-5 wk of age, accumulating at the peri-islet Schwann cell (pSC) border; the autoimmune destruction of the pSC mantle is extensive by 8 wks of age, 2 months before the onset of overt diabetes (Winer et al., 2003). In NOD$^{caps}$ mice, islet infiltrations were significantly reduced, compared with NOD$^{ctrl}$ (FIG. 1d, p<0.0001). More than 70% of NOD$^{caps}$ islets were free of lymphocytes by age 20 wk, whereas even in non-diabetic NOD$^{ctrl}$ mice of that age very few islets were lymphocyte-free (FIG. 1d). In one third of NOD$^{caps}$ mice, infiltrated islets were entirely absent, as demonstrated by extensive, serial sectioning. In the remaining two thirds of NOD$^{caps}$ mice, most islets remained free of lymphocytes, with some degree of inflammation in rare islets, but, strikingly, there was little of the typical insulitis progression over time (FIG. 1e). Corresponding to the reduction of T cell infiltrations, neonatal capsaicin treatment delayed the onset of diabetes (p=0.0002) and reduced its incidence (FIG. 1f, p<0.0001, 35 wk, n=52 mice/group, life table analysis). No further NOD$^{caps}$ mice developed disease over the next 12 wk, with about 80% reduction in final diabetes incidence (p<0.0001, Fisher's exact test).

It was observed that NOD mice spontaneously develop a Sjögren-like disease (sialitis/lacrimitis) which is under genetic controls separate from diabetes (Boulard et al., 2002; Cha et al., 2002). NOD$^{caps}$ mice exhibited the same submandibular lymphocyte infiltrates as untreated controls (FIG. 11). Capsaicin treatment thus causes a dramatic reduction in pancreatic islet inflammation and development of diabetes without a generalized effect on autoimmune infiltrations elsewhere in the NOD mouse.

Figure 13:
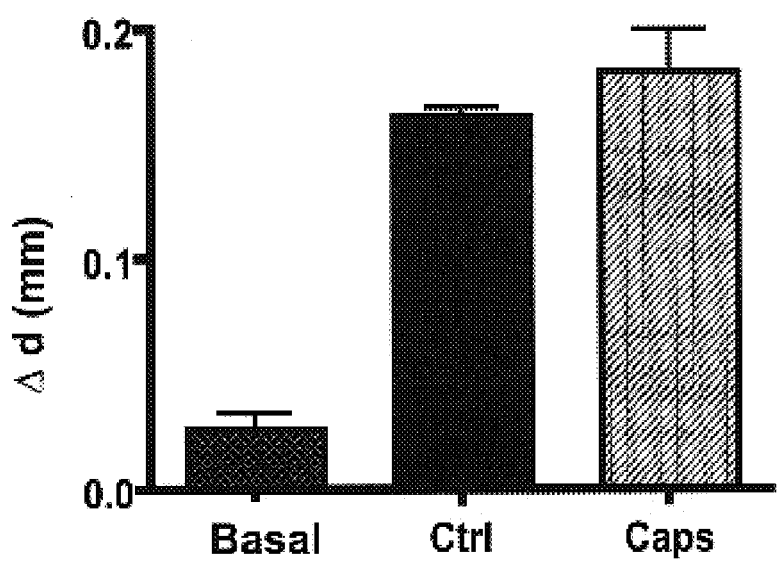
FIG. 13 illustrates chemically induced delayed hypersensitivity (DTH) responses in NOD$^{ctrl}$ and NOD$^{caps}$ mice.

The observed effects of capsaicin treatment on islet infiltration and disease development could either reflect a failure to generate islet autoreactive T cell pools, a block of tissue accumulation for relevant immune cell pools or a change in regulatory mechanisms. Capsaicin was reported to affect some immune functions in other animal models (Chancellor-Freeland et al., 1995; Helme et al., 1987; Nilsson et al., 1991; Santoni et al., 1996). To investigate the possible effect of capsaicin on immune functions or development in the NOD mouse, we compared systemic (FIG. 2a-e) and pancreatic T cells (FIG. 2f-i) in NOD$^{caps}$ and NOD$^{ctrl}$ mice. Systemic T cell pools autoreactive to islet- (Insulin, GAD65), pSC- (GFAP, S100b) and other disease-associated antigens (HSP60, BSA), were indistinguishable in NOD$^{caps}$ and NOD$^{ctrl}$ spleen cells (FIG. 2a). To probe the development of autoreactive T cell pools in NOD$^{caps}$ mice, we measured the peripheral frequency of a prevalent population of diabetogenic CD8+ T cells that recognizes residues 206-214 of islet-specific glucose 6 phosphatase catalytic subunit protein (IGRP) and its homologous, higher avidity mimotope NRP-V7 (Amrani et al., 2001; Amrani et al., 2000; Anderson et al., 1999; Lieberman et al., 2003; Verdaguer et al., 1997; Verdaguer et al., 1996). The size of the circulating NRP-V7-reactive CD8+ T cell pool was similar in NOD$^{caps}$ and NOD$^{ctrl}$ spleens (0.25±0.1%, p=0.69) (FIG. 2d). Lymphoid organ cellularities, T cell development and subset distributions were also not different in NOD$^{caps}$ and NOD$^{ctrl}$, comparing splenocytes, axillary lymph nodes and thymes (FIG. 12A-12D). Delayed type hypersensitivity reactions developed normally in NOD$^{caps}$ mice (FIG. 13), suggesting the maintenance of antigen presentation and of effector cell generation (Cua et al., 1995; Morikawa et al., 1993).

In contrast, pancreatic NOD$^{caps}$ lymph node tissue contained significantly reduced proportions and absolute numbers of CD8+ and of activated CD8+ CD69+ effector T lymphocytes, cells critical for islet destruction (DiLorenzo et al., 1998) (FIG. 2f, g). As a hallmark of prediabetes progression, prediabetic NOD mice selectively lose CD4+ CD25+, and Foxp3+ regulatory T cell subsets in pancreatic lymph node tissue (Bluestone and Tang, 2005; Pop et al., 2005). However, NOD$^{caps}$ mice maintained their regulatory T cell compartment in pancreatic lymph nodes beyond 12-16 wk of age (FIG. 2h, i). Thus, there are significant differences in the pancreatic, local immune system of NOD$^{caps}$ and NOD$^{ctrl}$ mice, consistent with the suppression of chronic progressive islet inflammation in these animals.

Figure 14:
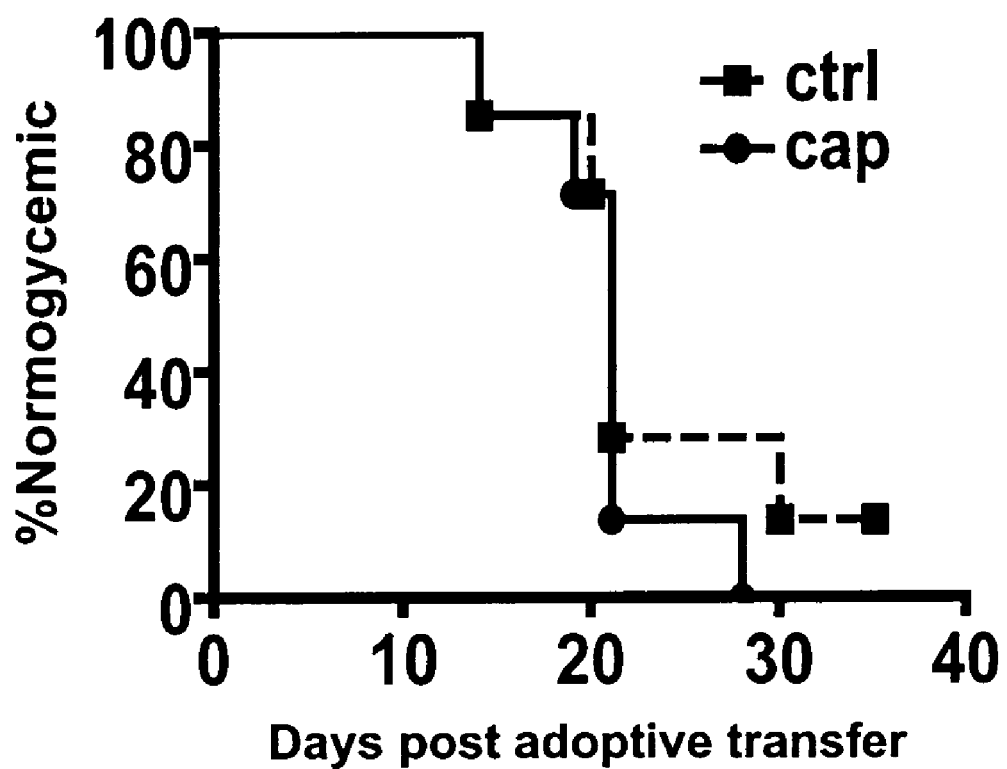
FIG. 14 demonstrates diabetes transfer efficiency of splenocytes from NOD$^{ctrl}$ or NOD$^{caps}$ mice when transferred i.v. to untreated NOD.scid mice.

Conceivably, undetected abnormalities in the NOD$^{caps}$ immune system might have influenced T cell pathogenicity and diabetes development. However, NOD$^{caps}$ animals that did develop disease showed insulitis and spleen cells from these animals transferred T1D with normal kinetics to lymphocyte-free NOD.scid recipients that were not treated with capsaicin (FIG. 14).

We also compared the ability of splenocytes from randomly selected NOD$^{caps}$ and NOD$^{ctrl}$ to initiate insulitis in such NOD.scid mice. NOD$^{caps}$ and NOD$^{ctrl}$ splenocytes initiated insulitis equally (FIG. 2c). Moreover, we analyzed BDC2.5 T cell receptor transgenic NOD mice treated with capsaicin (BDC2.5$^{caps}$) (Ji et al., 1999). Splenocytes from these animals similarly transferred T1D to untreated NOD$^{ctrl}$ mice (p>0.1).

Figure 15:
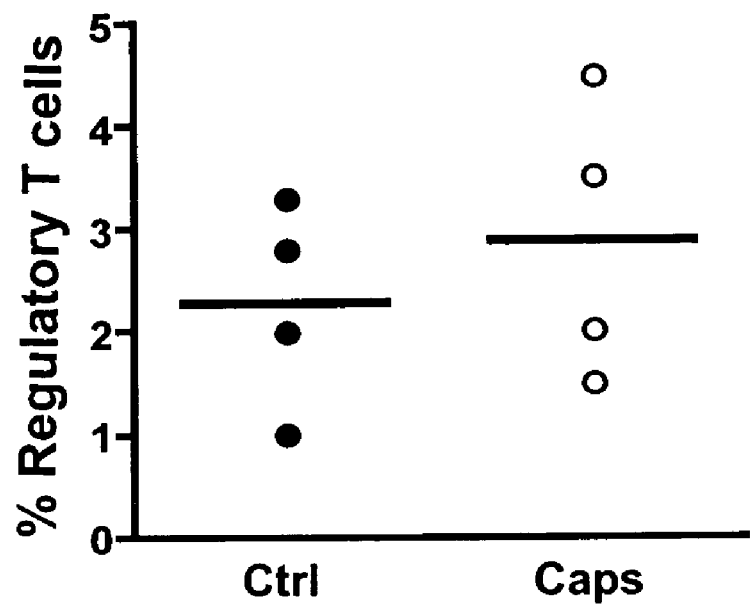
FIG. 15 illustrates the percentage of regulatory T cells in pancreatic lymph nodes after cyclophosphamide induced Type 1 diabetes.

Low dose cyclophosphamide accelerates NOD diabetes by multiple mechanisms (Hadaya et al., 2005). Low dose cyclophosphamide accelerated diabetes development in both NOD$^{caps}$ and NOD$^{ctrl}$ (p=ns, FIG. 2e) and was associated with reversal of the regulatory T cells accumulation present previously in NOD$^{caps}$ vs. NOD$^{ctrl}$ pancreatic lymph nodes (FIG. 15). Thus, NOD$^{caps}$ mice retain the principal ability to generate diabetogenic T cell pools.

Collectively, our observations separate loss of self-tolerance from target tissue invasion as distinct elements of T1D pathogenesis and they demonstrate that the NOD$^{caps}$ immune system retains pathogenic potential. TRPV1$^+$ sensory neurons thus appear critical for the immune cell accumulation in the pancreas.

NOD TRPV1 is Polymorphic

The above findings identify an important role of TRPV1+ primary afferent neurons in the initiation and progression of islet inflammation and T1D. TRPV1 maps to the Idd4.1 NOD diabetes-risk sublocus on mouse chromosome 11, into an approximately 0.3 cM interval downstream of D11Ndsl (FIG. 3a) (Grattan et al., 2002; Ivakine et al., 2005; McAleer et al., 1995).

Congenic replacement of the NOD Idd4 locus with the homologous B6 genomic interval protects from insulitis and, consequently, diabetes, although splenocytes from these congenic animals transfer both, insulitis and diabetes to NOD-.scid mice (Grattan et al., 2002). The NOD Idd4 risk locus differs from the homologous genomic region in the insulitis- and diabetes-resistant NOR strain, that carries nearly 90% of the NOD genome, including histocompatibility genes and most other T1 D risk loci (Ivakine et al., 2005; Serreze et al., 1994).

Figure 3:
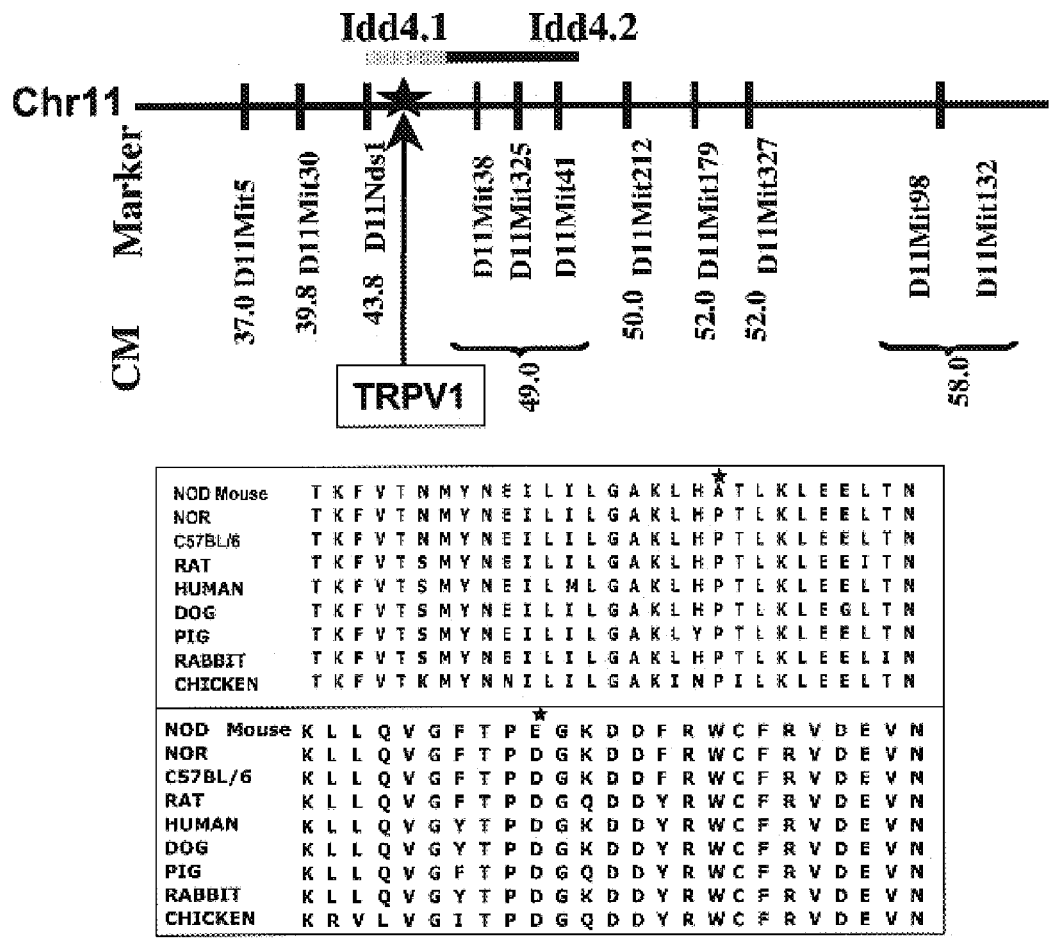
FIG. 3 illustrates that TRPV1 maps to the Idd4.1 NOD diabetes risk dublocus of mouse chromosome 11, and further illustrates the two in-frame base exchanges characteristic to the NOD sequence; (SEQ ID NOS 1-18,respectively, in order or appearance)

We cloned and sequenced TRPV1 cDNA from NOD and NOR mouse dorsal root ganglia (DRG), and confirmed selected sequence regions in NOD and NOR genomic DNA. The NOR TRPV1 was identical to the published wild type (B6 and DBA) sequence, but the NOD sequence has two in-frame base exchanges, leading to predicted $P_{322}$->$A_{322}$ and $D_{734}$->$E_{734}$ amino acid replacements (FIG. 3). Both replacements fall into regions highly conserved among diverse species (FIG. 3).

TRPV1$^{NOD}$ is Dysfunctional

Figures 4A, 4B, 4C, 4D, 4E, 4F:
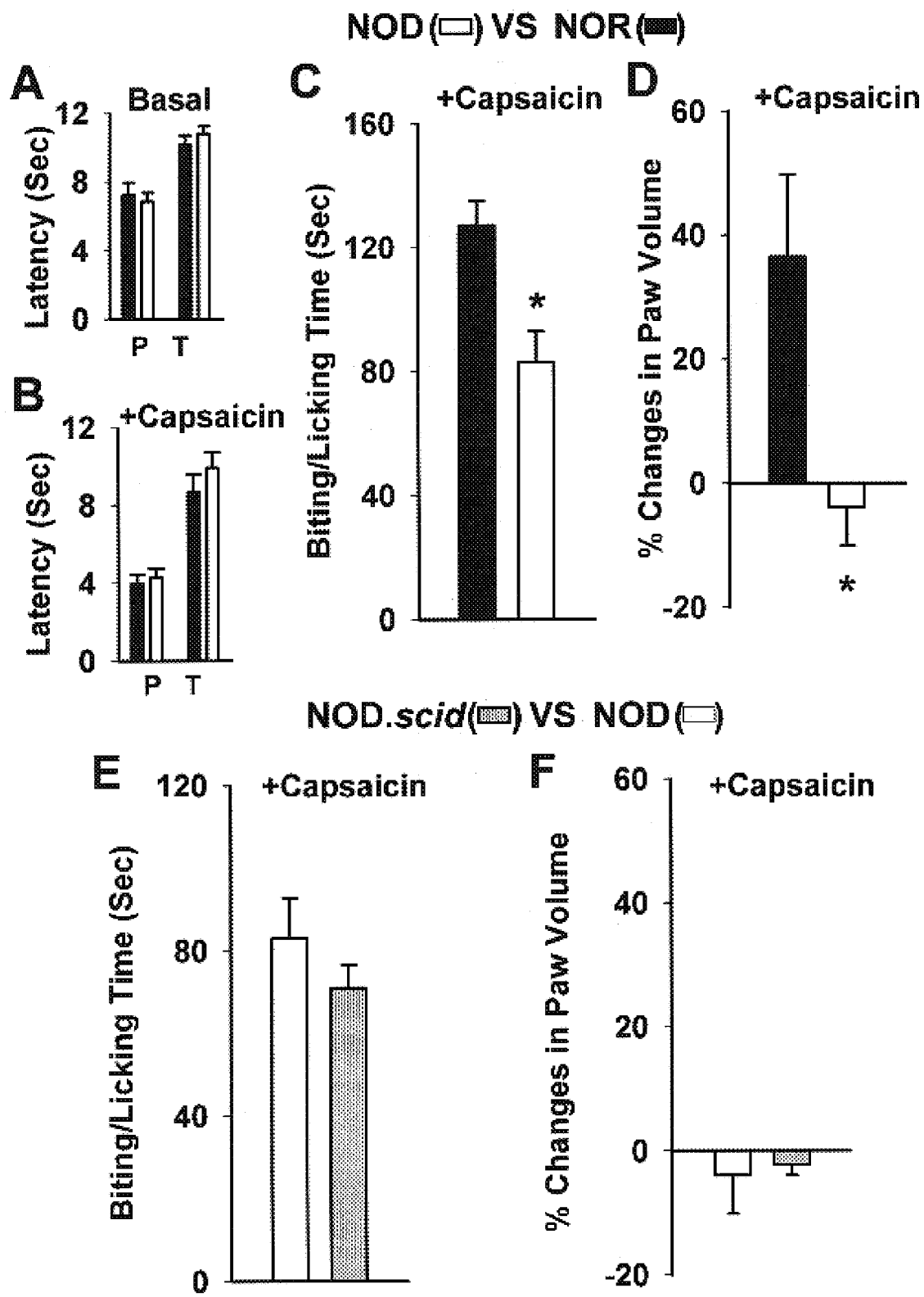
FIGS. 4A-4F illustrate the results of whole animal experiments in which TRPV1+ sensory afferents were stimulated by subcutaneous capsaicin application in NOD and NOR mice.

Further investigation allowed us to determine whether the sequence differences in TRPV1$^{NOD}$ might cause abnormalities of TRPV1 function. The innervation of skin by TRPV1$^+$ sensory afferents allowed assessment of potential functional differences by whole-animal experiments in which these afferents were stimulated by cutaneous capsaicin application (FIG. 4). Before testing capsaicin we found that there were no differences between NOD and NOR mice in basal withdrawal responses to heat stimulation of the paw or tail (FIG. 4a), indicating that there was no generalized alteration of basal nociception in NOD mice. In addition, the sensitization of heat-evoked withdrawal responses following intradermal capsaicin administration was not different in NOD versus NOR mice (FIG. 4b). However, nociceptive behavioral responses (biting, licking) evoked by intradermal capsaicin were markedly depressed in NOD as compared with NOR mice (p<0.05, FIG. 4c). Similarly, the paw edema produced by capsaicin was significantly reduced in NOD mice (p<0.01, FIG. 4d), suggesting reduced neuropeptide secretion and inflammation at the site of stimulation.

The depressed NOD acute nociceptive and neurogenic inflammatory responses were not due to ongoing autoimmune inflammation, since NOD.scid mice, which lack lymphocytes, were not different from NOD (FIG. 4e, f). Thus, the TRPV1$^{NOD}$ sequence abnormality appears to produce dysfunction of TRPV1-mediated responses to capsaicin.

Figures 5A, 5B, 5C, 5D, 5E, 5F:
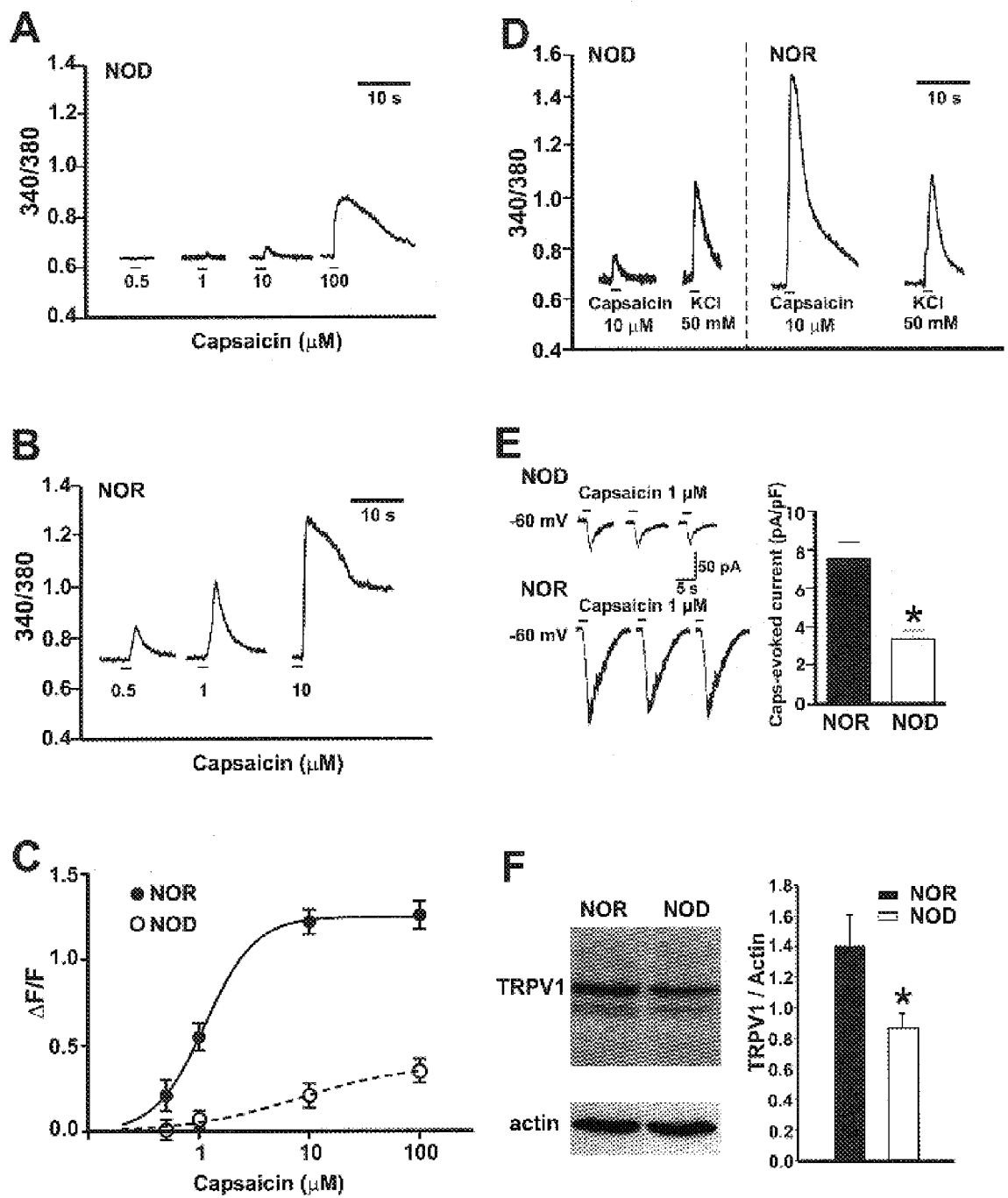
FIGS. 5A-5F illustrate assessment of TRPV1 function by recordation of capsaicin-evoked $Ca^{2+}$ responses in dorsal root ganglion (DRG) neurons from NOD and NOR mice.

To assess TRPV1 function more directly, we recorded capsaicin-evoked $Ca^{2+}$ responses in dorsal root ganglion (DRG) neurons from NOD and NOR mice (FIG. 5). The maximum NOD DRG $Ca^{2+}$ response to capsaicin was significantly smaller than that of NOR DRG neurons ($p<0.01$, FIG. 5a-c). In addition, the maximum capsaicin response was reduced and required 10-fold higher drug concentrations in NOD DRG neurons, compared with that in NOR ($p<0.05$, FIG. 5c). In contrast, KCl-evoked $Ca^{2+}$ responses of NOD and NOR DRG neurons were not different (FIG. 5d), indicating that NOD mice do not exhibit a general abnormality in $Ca^{2+}$ responsiveness.

The most direct readout of TRPV1 function are stimulus-evoked current responses, and we found that capsaicin-evoked whole-cell currents were significantly smaller in DRG neurons from NOD mice as compared with NOR mice (FIG. 5e).

Because of the depressed TRPV1 function, we measured TRPV1 protein expression in DRGs and found that the basal TRPV1 protein level in NOD mice was lower than that in NOR (FIG. 5f). Thus, the depression of capsaicin-evoked $Ca^{2+}$ and current responses in DRG neurons from NOD mice may in part reflect decreased steady-state expression levels of $TRPV1^{NOD}$. The right-ward shift in the capsaicin concentration-response relationship suggests that the functionality of the $TRPV1^{NOD}$ protein itself may also be reduced as compared with $TRPV1^{wild\ type}$. Collectively, we discovered functional abnormalities in nociceptive behavior, neurogenic inflammation, channel function and expression which define $TRPV1^{NOD}$ as a hypo-functional mutant.

Localized Pancreatic Substance P Administration Reverses Islet Pathology

Figure 16:
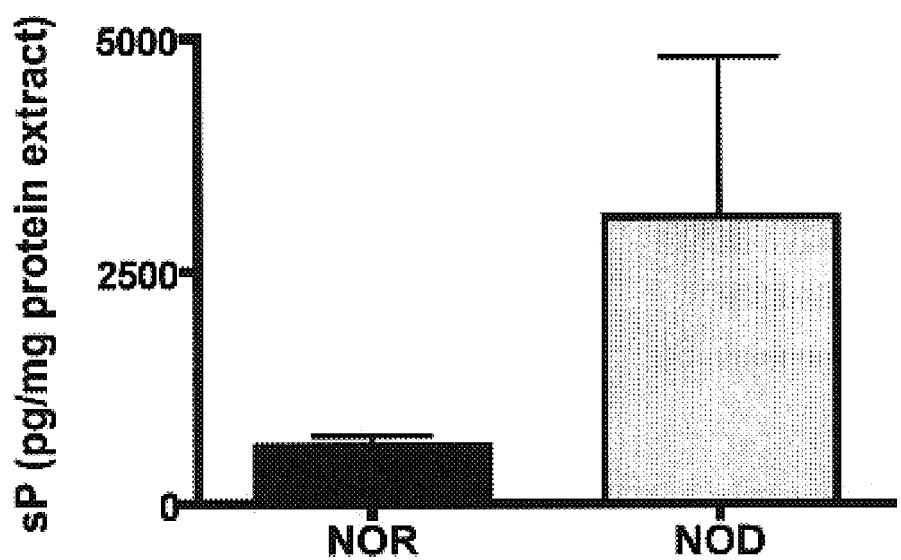
FIG. 16 illustrates that the DRG levels of the neuropeptide, substance P (sP) were elevated in NOD compared to NOR mice.

We reasoned that abnormal TRPV1 function might selectively lead to islet pathology, if there was a local, disease-predisposing TRPV1 effect on β-cell function, and if that effect was removed in $NOD^{caps}$ mice. The insulin-rich islet milieu represents a unique environment for TRPV1+ nerve terminals, as they express insulin receptors and insulin sensitizes and lowers the activation threshold of TRPV1 channels (Van Buren et al., 2005). Based on the diminished capsaicin-evoked neurogenic inflammation in NOD mice, and the reduced TRPV1 expression and function, we hypothesized that release of mediators of neurogenic inflammation from the peripheral terminals of sensory neurons may be depressed in these mice. One of the principal mediators of neurogenic inflammation is the neuropeptide, substance P (sP) (O'Connor et al., 2004), and consistent with reduced release we found that sP levels were elevated in NOD compared with NOR dorsal root ganglia, the location of substance P synthesis (FIG. 16). $NOD^{ctrl}$ pancreas shows accumulation of more sP in nerve endings than B6 mice and this is not due to inflammation as it was also observed in NOD.scid mice (FIG. Sx). The enhanced accumulation of sP is consistent with reduced sP release.

Figures 6A, 6B, 6C, 6D, 6E, 6F, 6G, 6H, 6I:
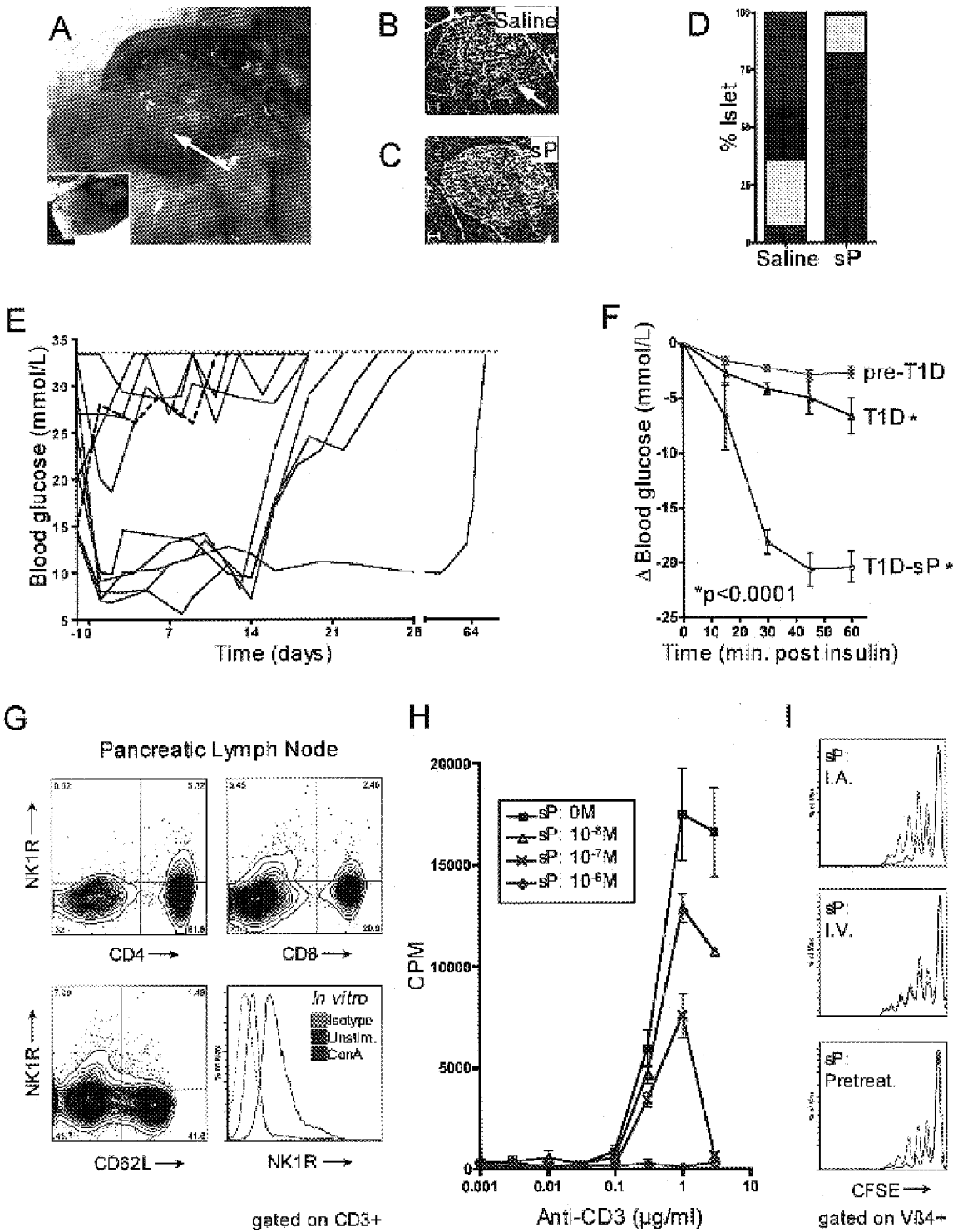
FIG. 6A demonstrates the selective delivery of intra-arterially (i.a.) injected Evans Blue dye to pancreatic and pancreatic lymph node tissue.
FIGS. 6B and 6C illustrate that in prediabetic NOD$^{ctrl}$ animals, sP injection resulted in clearing of islet T cell infiltration.
FIG. 6D illustrates that in animals receiving only pancreatic vehicle injection, only 6% were lymphocyte free.
FIG. 6E demonstrates that after sP administration, and without insulin therapy, over half of the i.a. injected diabetics normalized blood glucose levels.
FIG. 6F illustrates that raising pancreatic sP levels enhanced insulin sensitivity.
FIG. 6G illustrates NK1R expression on a portion of T cells from pancreatic lymph nodes.
FIG. 6H demonstrates sP response of activated CD4+ NOD T cells in vitro; and illustrates that substance P abrogated cell proliferation and survival in a dose-dependent fashion.
FIG. 6I illustrates that systemic injection of sP did not have a similar effect.

If depressed sP release was critical for NOD islet pathology, then increasing pancreatic sP levels is predicted to relieve the pathogenic process. We therefore injected sP via the pancreatic artery. FIG. 6a demonstrates the pancreatic delivery of intra-arterially (i.a.) injected Evans Blue dye, including a pancreatic lymph node (insert). In prediabetic NOD animals, 12 wk of age, we found that within 2d after i.a. sP injection (2 nmoles/kg), about 80% of all islets were free of T cell infiltration (FIG. 6b, c), and there were only small, residual infiltrates in the remainder. Systemic (i.v.) injection of the same sP dose did not have similar effects (see below, FIG. 6i). In animals receiving pancreatic i.a. vehicle injection, only 6% of islets were lymphocyte free ($p<0.0001$) (FIG. 6d).

Figure 18:
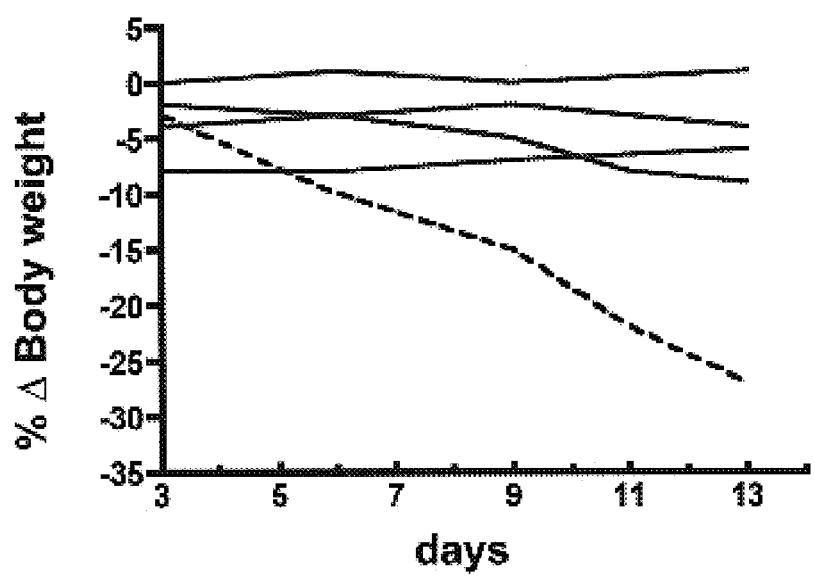
FIG. 18 demonstrates that even in mice that failed to reverse hyperglycemia, i.a. sP resulted in significant improvement of metabolic control.

Analogous observations were made following pancreatic i.a. injection of sP into newly diabetic NOD mice, 2-3 d after diagnosis. Following sP administration, and without insulin therapy, over half of the i.a. injected diabetics normalized blood glucose levels (FIG. 6e, red lines). In these responding mice, fasting blood glucose returned to near normal levels rapidly and remained at these levels for 2-8 wk. Raising pancreatic sP levels dramatically enhanced insulin sensitivity, suggesting that the elevated insulin resistance at diagnosis was normalized (FIG. 6f). On average, mice that reversed diabetes had less extreme hyperglycemia at the time of diagnosis than did the non-responding mice, likely reflective of a larger residual β-cell mass at the time of sP administration. However, even in mice that failed to reverse hyperglycemia (blue lines), i.a. sP caused a significant improvement of metabolic control, preventing the progressive loss of body weight typical of overtly diabetic NOD mice (FIG. 18). This improvement corresponds to significantly ($p<0.0001$) improved insulin sensitivity (FIG. 6f, blue line) which enhances the effectiveness of a small remaining b-cell mass at diabetes onset. In all vehicle-injected control animals, blood glucose rose progressively, body weights declined and animals were sacrificed because of severe diabetes between days 12-16.

Abundant expression of the NK1R sP receptor has been reported for islet infiltrating lymphocytes (Persson-Sjogren et al., 2005), and, therefore, one likely target for sP is activated pancreatic T cells. We detected NK1R expression on a portion of T cells from pancreatic lymph nodes (FIG. 6g), however, upon in vitro activation with Con A, essentially all NOD splenic T cells expressed NK1R (FIG. 6g, insert). To determine the functional effect of NK1R ligation, we tested the sP response of activated CD4+ NOD T cells in vitro. Substance P abrogated cell proliferation and survival in a dose-dependent fashion (FIG. 6h).

To determine the in vivo effect of pancreatic i.a. sP injection on clonal T cell expansion in pancreatic lymph node, we used islet reactive, BDC2.5 T cell receptor transgenic T cells after labeling with the fluorescent dye, CFSE (Ji et al., 1999). Cells were transferred into 12 wk-old, normoglycemic NOD females which had received pancreatic i.a. or systemic i.v. sP (red lines) or vehicle injections 12-16 hr prior (FIG. 6i). BDC2.5 T cells from pancreatic lymph nodes were analyzed by flow cytometry 4 days later. Injection of sP reduced cellularity and clonal expansion, measured by dye dilution ($p=0.003$). Systemic (i.v.) injection of the same sP dose had no effect on expansion of BDC2.5 T cells in pancreatic lymph nodes, suggesting a pancreas tissue-conditioning effect of i.a. pancreas injection that lasts at least 12-16 hr. A third set of animals received BDC2.5 cells that were in vitro pretreated with sP or vehicle overnight. This in vitro pretreatment with sP, reduced the ability of these cells to expand in pancreatic lymph nodes (6i, bottom panel, $p=0.0045$). As equal numbers of viable cells were transferred, these observations imply that sP also has a T cell conditioning effect.

Taken together, the data suggest that reduced neuropeptide release by pancreatic TRPV1+ nerve terminals is a pathogenic event in NOD diabetes, amenable to therapeutic correction.

Figure 17:
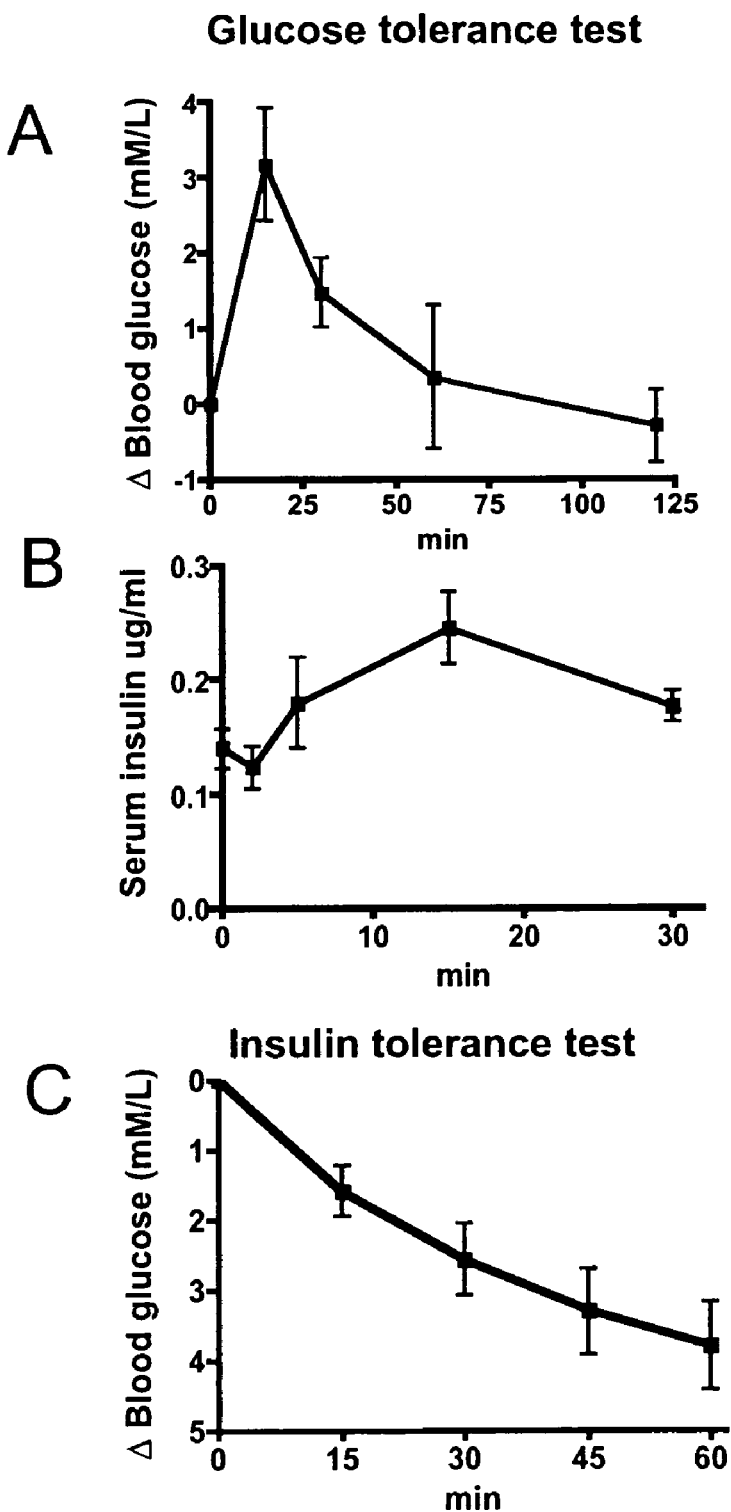
FIGS. 17A-17C glucose metabolism in CD-1 mice.

TRPV1 Function and b-Cell Stress

β-cell stress has previously been suggested as an early element of T1D pathoetiology, thus an additional objective of this work became the determination of whether the hypofunctional TRPV1$^{NOD}$ is related to signs of b-cell stress, hyperinsulinism and abnormal glucose clearance, observed even in young NOD mice (Rosmalen et al., 2000; van de Wall et al., 2005). We compared measures of β-cell function in untreated and in capsaicin treated NOD.scid mice, and in C57/BL6J ('B6') and B6.TRPV1$^{-/-}$ mice, the latter with a normal complement of sensory afferent neurons but absent TRPV1 expression (Caterina et al., 2000). NOD.scid mice were used to ascertain absence of lymphoid islet infiltration in NOD experiments, CD1 mice provided controls (FIGS. 17A-17C).

Figure 7:
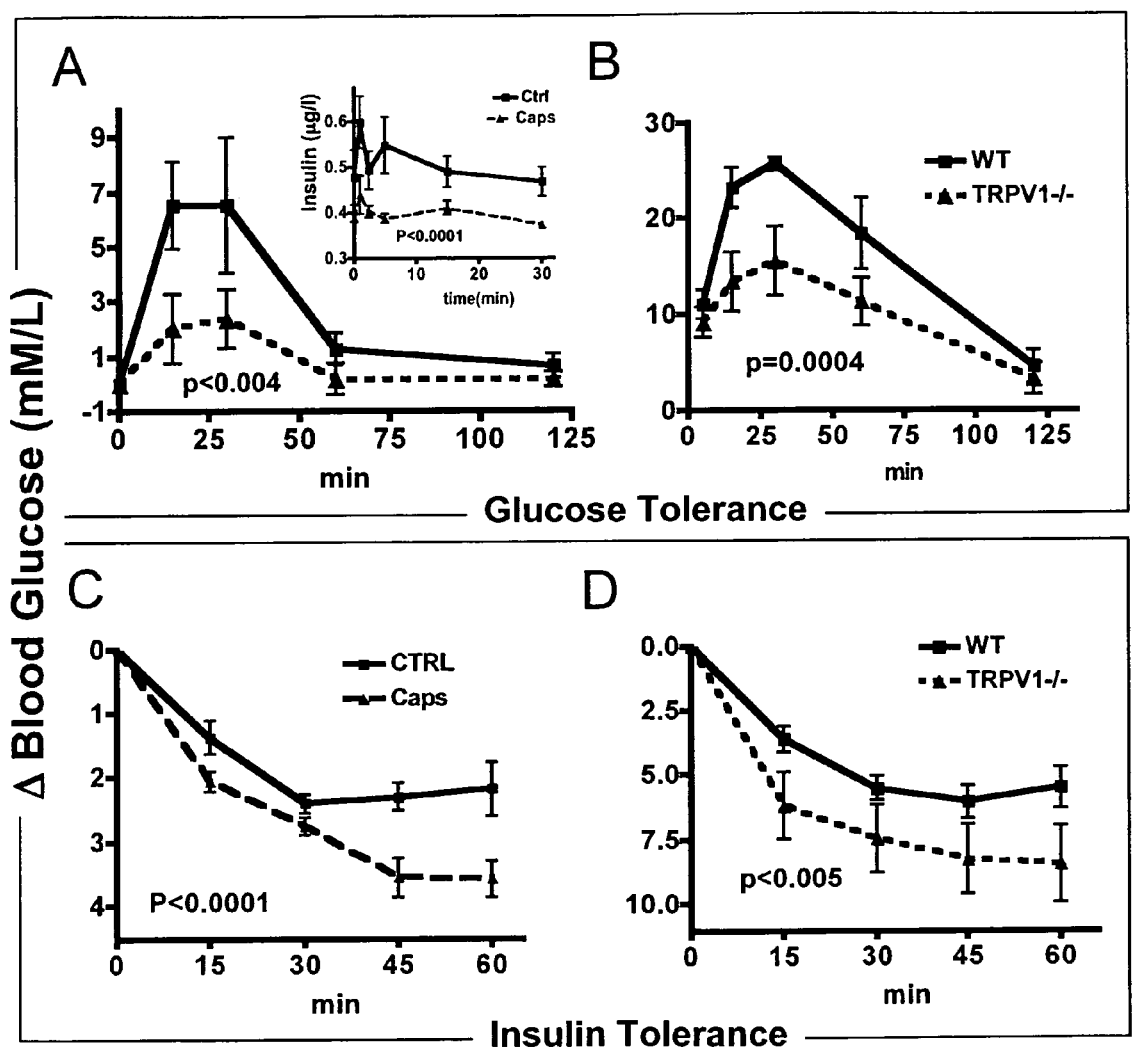
FIG. 7A-7D illustrate differences in glucose and insulin tolerance between NOD.scid$^{ctrl}$ versus NOD.scid$^{caps}$ mice.

The high-normal serum glucose levels after i.p. glucose challenge in 10-12 wk old NOD.scid$^{ctrl}$ mice were significantly reduced in NOD.scid$^{caps}$ mice (FIG. 7a, p=0.004). The improved NOD.scid$^{caps}$ glucose response was associated with significantly less insulin production (FIG. 7a, insert), suggesting more effective insulin action following removal of TRPV1$^+$ sensory neurons.

B6 mice develop elevated insulin resistance and type 2 diabetes-like disease (Parekh et al., 1998), attributed to the functional deletion of nicotinamide transhydrogenase (Freeman et al., 2006). Consistently, we observed high blood glucose levels after standard i.p. glucose challenge (FIG. 7b). B6.TRPV1$^{-/-}$ mice showed a significantly improved glucose response, analogous to NOD$^{caps}$ mice, further pointing to the possibility that TRPV1 may play a general role in β-cell physiology.

To more directly assess if both data sets could reflect enhanced insulin sensitivity due to TRPV1 removal, we measured glucose clearance after a single insulin injection. Compared to their respective control animals, NOD$^{caps}$ and B6.TRPV1$^{-/-}$ mice showed significantly enhanced and accelerated glucose clearance, which we interpreted as evidence for reduced insulin resistance due to the absence of TRPV1 in these two independent animal models. Similar outcomes in NOD$^{caps}$ and B6.TRPV1$^{-/-}$ mice link the observed effects on β-cell function to TRPV1. Enhanced insulin resistance associated with TRPV1$^{NOD}$ constitutes a persistent β-cell stress, likely worsening with progressive islet inflammation (Nielsen et al., 2004). TRPV1 and TRPV1+ sensory neurons impact insulin homeostasis in these models of Type 1 and Type 2 diabetes.

Congenic Replacement of NOD.Idd4

As a test of our conclusions that TRPV1 plays a fundamental role in islet inflammation and insulin homeostasis, we investigated NOD.B6.Idd4-congenic mice (FIG. 8). These mice carry wild type TRPV1 in this locus, and are insulitis- and diabetes resistant despite the fact that their splenocytes transfer diabetes to NOD.scid mice (Grattan et al., 2002). Consistent with wild type TRPV1 function, we found that these congenics have normalized behavioral responses to cutaneous capsaicin injection (biting/licking, FIG. 8a), neurogenic inflammation following paw injection with capsaicin (FIG. 8b) and Ca$^{2+}$ responses in capsaicin-stimulated DRG (FIG. 8c). The glucose responses of weaned Idd4 congenics were comparable to those in NOD control mice, however, there was a significant reduction in glucose-induced insulin secretion, suggesting an absence of elevated insulin resistance in these animals (FIG. 8d).

These NOD congenic mice resemble NOD$^{caps}$ mice, as both are insulitis/diabetes protected, although their T cells transfer diabetes to NOD.scid recipients. TRPV1$^{NOD}$ adds elevated insulin resistance as new, strikingly diabetes-relevant phenotype to the NOD Idd4.1 risk locus, presently associated only with insulitis; transgenic rescue experiments will be required for formal proof that TRPV1 is or is not the Idd4.1 diabetes risk gene.

Experimental Methods

Mice

NOD, NOD.scid, BDC2.5 TCR transgenic NOD mice ('BDC2.5-NOD'), NOD-β2m$^{null}$, C57BL/6 ('B6'), B6-TRPV1$^{null}$, NOR NOD×B6 Idd4 congenic mice (NOD.B6-(D11Nds1-D11Mit325)/DelJ) were obtained from the Jackson Laboratories (Bar Harbor, Me.) and maintained under approved protocols in our vivarium (NOD female diabetes incidence: 85-90%). For removal of TRPV1$^+$ neurons, 50 mg/kg capsaicin (20 μL, Sigma, St. Louis, Mo.) was subcutaneously injected into 2d-old mice with no signs of adverse effects (NOD$^{caps}$). Control mice (NOD$^{ctrl}$) received 20 μL vehicle (10% ethanol, 10% Tween, 80% saline). In adoptive transfer experiments, splenocytes from 4-6 diabetic NOD females were pooled and 10$^7$ cells/mouse were injected (100 μL i.v.) into irradiated (300 rad) 6- to 8 wk-old NOD.scid recipients. Diastix strips were used to screen for glucosuria (Bayer HealthCare), diabetes was confirmed by diabetic blood glucose measurements on 2 consecutive days (>13.8 mM/l; SureStep, Life Technologies Inc., Burnaby, British Columbia, Canada).

Delayed type hypersensitivity (DTH): DTH responses were elicited after sensitizing 6 wk old mice with 7% TNCB in 4:1 (vol/vol) acetone/olive oil. Abdomens were shaved and 100 μl of the allergen were applied. 6 d later, the baseline thickness of right ears were measured by gauge before application of 10 μl 1% TNCB in oil or carrier only. Ear thickness was re-measured in sensitized and naïve animals 24 hr later.

T-Cell Studies

Splenocytes from 3- to 24 wk-old NOD females were cultured (4×10$^5$ cells/well) in AIM V serum-free medium (Life Technologies) containing antigen (0.002-50 μg/ml), baculovirus-derived human GAD65 (Diamyd Diagnostics, Stockholm, Sweden), human GFAP (>90% pure) and bovine S100b (>98% pure; Calbiochem, San Diego, Calif.) were purchased, other antigens were previously generated and described (Winer et al., 2003). After 72 hrs, cultures were pulsed (1 μCi, [3H]thymidine/18 hrs) and counted by liquid scintillation. Lymph node assays were similar, but used 2×10$^5$ lymph node cells plus 2×10$^5$ irradiated (1,100 rad), syngeneic splenocytes/well. To normalize pooled data, we calculated a stimulation index (SI, cpm antigen stimulated/medium control), background counts were <1500 cpm in spleen cell and <1000 cpm in lymph node cultures. In some proliferation studies, plate-bound anti-CD3 (0.001-3 μg/ml; BD PharMingen) and anti-CD28 (0.2 μg/ml; BD PharMingen) were used to stimulate CD4+ T-cells negatively selected from NOD β2m$^{null}$ splenocytes in the presence of substance P.

Intra-Arterial Pancreas Injection

Animals were anaesthetized with isoflurane and the aorta developed with minimal trauma to ligate above and below the celiac artery. A 32G needle was used to inject Evans Blue (3 mg/kg/100 μl; Sigma), substance P (2 nmol/100 μl; Sigma) or saline into the aorta just prior to the celiac branching. Ligations are released after closure of the injection site. For insulitis studies, pancreata from treated mice were obtained 48-72 hr after pancreas injection treatment and histology performed. In diabetes reversal experiments, newly diagnosed NOD female mice were treated with either saline or substance P and followed without exogenous insulin treatment.

5- and 6-carboxyl-fluorescien Succimidyl Ester (CFSE) Labeling

For dye dilution in vivo clonal expansion studies, splenic CD4+ T-cells from NOD-BDC2.5 females were isolated by negative selection (Stemcell Technologies, Vancouver, Canada) and incubated with 2.5 µM CFSE (10'/37° C., Molecular Probes, Eugene, Oreg.) in PBS. Prediabetic (12 wk) NOD females pretreated 12 hr prior with substance P or saline, were injected i.v. with 3×10⁶ CFSE-labeled CD4+ T-cells in sterile PBS.

Immunofluorescence and Histology

Frozen murine pancreas sections were fixed in 4% paraformaldehyde, blocked with 5% normal donkey serum (Jackson), and stained with polyclonal rat or goat antibodies against GFAP (Signet Pathology Systems, Dedham, Mass.), polyclonal rabbit anti-TRPV1 (Oncogene) or guinea-pig antibody against insulin (DAKO, Carpinteria, Calif.). Bound antibodies were detected with biotinylated donkey anti-guinea pig or rat IgG (1:200, Jackson), Streptavidin AlexaFluor 546 or 633 (1:300, Molecular Probes, Eugene, Oreg.), and FITC conjugated donkey anti-rabbit IgG (1:25, Jackson). When the biotin-streptavidin system was used, sections were also blocked using an avidin/biotin blocking kit (Vector, Burlingame, Calif.). TRPV1 staining was performed on snap-frozen sections of NOD female pancreas with an overnight incubation of primary antibody at 4° C. To score insulitis severity, pancreata were fixed in 10% buffered formalin for a minimum of 24 hr. Histological sections were stained with hematoxylin and eosin and three blinded observers scored at the following scale: 0, normal islet; 1, peri-insulitis or encroachment of <25% of the islet surface area; 2, infiltration of 25-50% of the islet surface area; 3, infiltration of >50% of the islet surface area (Winer et al., 2003). Spleen and lymph node cells were stained with either 2 nM PE-conjugated NRP-V7/H-2$K^d$ or TUM/H-2$K^d$ tetramers, the latter a negative control, in FACS buffer (1% v/v FBS, 0.1% w/v NaN₃ in PBS) at 4° C. for 1 hr, followed by staining with FITC-conjugated anti-CD8 mAb (clone 53-6.7; 5 µg/µL) and PerCP-conjugated anti-B 220 Ab (clone RA6-3B2; 2 µg/µL, both from BD Pharmingen). Tetramer positivity was analyzed on gated CD8+B220− cells and reported as percentage of cells binding the NRP-V7/H-2$K^d$ tetramer minus the percentage of cells binding the negative control, TUM/H-2$K^d$ tetramer.

Flow Cytometry

Lymphocytes from thymus, pancreatic/axillary lymph nodes and spleen were stained with FITC, PE, and APC conjugated antibodies to CD3, CD4, CD8, CD44, CD25, CD69 CD62L and FoxP3 (BD Pharmingen, not all combinations are shown). NK-1R and Vβ4 antibodies were obtained from Novus Biologicals (Littleton, Colo.) and Cedarlane (Hornby, Canada), respectively. Live events were collected based on forward- and side-scatter profiles on a FACScan flow cytometer (BD) and analyzed using FlowJo software (Stanford University).

Molecular Cloning

PCR amplification was performed with cDNA from NOD, NOR, and B6 dorsal root ganglia using TRVP1 specific primers. Forward: 5'ATGGACAAATGGGCTACCTTAG3'(SEQ ID NO: 19), reverse: 5'TCATTTCTCCCCTGC-CCCCATGG3'(SEQ ID NO: 20). We cloned TRPV1 cDNA using the TOPO® XL PCR Cloning Kit (Invitrogen, Mississauga, ON). Genomic fragments of polymorphic TRPV1 regions were cloned using genomic DNA and the following primers:

5'ATGGAGAAATGGGCTAGCTTAG3' (SEQ ID NO:19),

5'TGTTGTCAGCTGTGTTATCTGCC3' (SEQ ID NO:21),

-continued

5'TTCAGCCATCGCAAGGAGTA3' (SEQ ID NO:22), and

5'TCATTTCTCCCCTGGGGCCATGG3' (SEQ ID NO:20), 3-5 independent clones from each mouse strain were sequenced with reproducible results.

RT-PCR: Trizol (Sigma) was used for mRNA extraction from tissues. RT reactions used SuperScript™ II RnaseH-reverse transcriptase (Invitrogen): forward primer: 5'-GGAGAAATGGGCTAGCTTAG-3', (SEQ ID NO: 23) reverse primer: 5'-GAAGACCTCAGCATCCTCTGG (SEQ ID NO: 24) (XL-PCR Applied Biosystems)

Behavioral Studies and Paw Volume Measurement

Male NOD, NOR, NOD.scid and NOD.B6.Idd4-congenic mice, 5-10 wk old, were used for behavioral and paw volume measurements. All behavioral tests were conducted between 9:00 and 16:00 hr. Before testing, mice were allowed to acclimatize to the testing environment for 30 minutes and to the testing apparatus for 1 hr. Paw thermal withdrawal thresholds were measured with a paw thermal stimulator system (UCLA, San Diego, Calif.). The stimulus current was maintained at 4.8 amperes while a 24 second cut-off was used to limit possible tissue damage. The tail-flick assay was conducted using a tail-flick analgesia meter (Columbus Instruments). Paw volumes were measured using a commercially available plethysmometer (Ugo Basile) and values were standardized by expression as a percentage of individual preinjection volumes, to accommodate the variation in body weights. Capsaicin (0.1 µg/10 µl) was injected s.c. into the plantar part of mouse hind paw. Capsaicin induced biting/licking time was recorded for the first 5 minutes. Paw withdrawal thresholds were measured 15 min following capsaicin, and paw volume was measured 45 min following capsaicin injection. NOD$^{caps}$ and NOD$^{ctrl}$ thermosensitivity was analyzed by standard heated (56° C.) plate assay, measuring time to biting/licking response.

Ca²⁺ Response Measurement

Dorsal root ganglia from male NOD, NOR mice and NOD.B6.Idd4-congenic (5-10 wk) were isolated and cultured in F12 medium (Invitrogen) with 10 ng/mL nerve- and 10 ng/mL glial-derived nerve growth factor. Cultures were used 3-5 d after plating. The Ca²⁺-sensitive fluorophore, fura-2 (Molecular Probes, Eugene, Oreg.), was used to assess [Ca²⁺]$_i$ by ratiometric measurement. Excitation (340 and 380 nm) was generated by a xenon arc lamp and passed through a high-speed, computer-controlled, variable-wavelength monochromator. This light was transmitted to the recording dish via a fiberoptic cable. Emitted light was directed through a 510 nm bandpass filter and detected by an intensified CCD camera. Image data were analyzed off-line. Each 340 nm image was divided, on a pixel-by-pixel basis, by the corresponding 380 nm image, producing a ratio. Averaged values of the ratios within each region of interest were plotted as a function of time.

Electrophysiological Recording of TPRV1 Currents

Whole-cell patch-clamp recordings were performed 3-5 d after preparation of DRG neurons. Standard bath solution contained (in mM): 140 NaCl, 5 KCl, 2 CaCl₂, 10 HEPES, and 10 glucose, pH 7.4 (adjusted with NaOH). Pipette solution contained (in mM): 140 CsF, 10 BAPTA, 1 CaCl₂, 2 MgCl₂, 10 HEPES and 4 K₂ATP, pH 7.3, osmolarity 300 mosM. All patch-clamp experiments were performed at room temperature. TRPV1 currents were recorded using an Axopatch 1-D amplifier, data were digitized with DigiData1322, filtered (2 kHz), and acquired by the pClamp9.0 program. Recordings in which the series resistance varied by more than 10% were rejected.

Immunoblotting

DRG or dorsal horns (spinal cord) were dissected and immediately frozen at −80° C. Upon thawing, they were homogenized in lysis buffer (in mM: 20 Tris, pH8, 137 NaCl, 2 EDTA, 1 sodium vanadate, 5 NaF, 1 phenylmethanesulfonyl fluoride (PMSF), glycerol 10%, Nonidet P-40 1%, SDS 1%, anti-pain 10 µg/mL, leupeptin 10 µg/mL, pepstatin 10 µg/mL, all Sigma) at 4° C. Total protein (45 µg DRG protein, 30 µg spinal cord) were electrophoresed (10% acrylamide gels), western blotted, probed overnight with rabbit anti-TRPV1 antibody (1:250, Oncogene) and developed with the ECL kit (Amersham). As a loading control for each lane, membranes were stripped and reprobed with mouse anti-β actin antibody (1:4000, Sigma). Densitometric analysis employed NIH Image-J software.

Statistics

All tests were 2-tailed, significance was set at 5%. Life tables, t-tests (flow cytometry), ANOVA and Fisher's exact test were used as described in the text.

CONCLUSIONS

In summary, in the different, independent animal strains and experimental conditions analyzed, TRPV1 emerges as a central controller of both islet stress and T cell infiltration. Elimination of TRPV1+ neurons by capsaicin, transient functional normalization by acute local sP injection or replacement with wild type TRPV1 in Idd4 congenics all have the same, islet-specific outcomes: normalized insulin sensitivity and abrogation of insulitis, despite unimpeded generation of autoreactive lymphocytes that can transfer disease to untreated NOD hosts.

Figure 19:
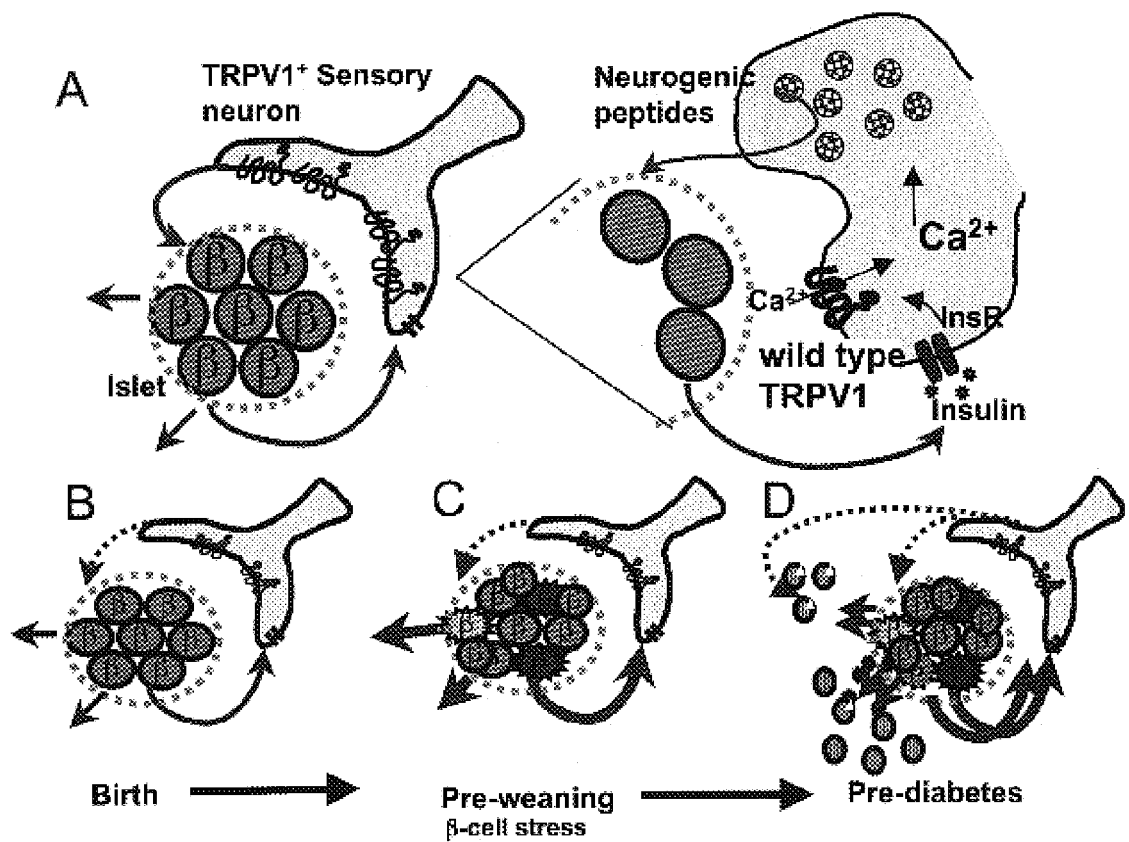
FIG. 19 illustrates the β-cell<-->TRPV1 regulatory circuit in NOD mouse T1D pathoetiology.

One explanation which unifies these observations is a local feedback interaction between β-cells and the primary sensory neurons innervating the islets (FIG. 19). Such a mechanism has been proposed previously based on more indirect evidence (Hermansen and Ahren, 1990). Normally, this interaction is in balance, but in the NOD mouse, hypofunction of TRPV1 unbalances the feedback, leading to β-cell stress and infiltration by autoreactive T cell pools independently generated in the NOD mouse. Removing TRPV1 neurons leads to elimination of the unbalanced, pathogenic interaction, while administering sP exogenously appears to re-normalize the interaction, at least transiently.

With specific reference to FIG. 19, islet insulin ligates insulin receptors on TRPV1+ sensory afferent islet terminals which lowers the activation threshold of TRPV1 with subsequent $Ca^{2+}$ influx and local release of neuropeptides (e.g. substance P, CGRP). Secreted mediators insulin production in a tonic balance. Our observations indicate that this balanced feedback loop is essential for normal β-cell homeostasis.

Neonatal capsaicin treatment suppresses NOD islet infiltration and local expansion of diabetogenic T-cells without detectable impairment of global T-cell function, including typical NOD autoreactivity. The treatment normalizes β-cell stress as measured through insulin sensitivity and glucose responses. We have mapped this effect to the $TRPV1^{NOD}$ gene in the Idd4 diabetes risk region, and shown that that $TRPV1^{NOD}$ is a hypo-functional mutant with considerable reduction in TRPV1 signaling, expression and downstream release of neuropeptides. Focusing on one major neuropeptide secreted by TRPV1+ neurons, sP, we demonstrate that sP has a direct deleterious effect on T cells, most expressing detectable NK1R sP receptors following activation.

A direct neuropeptide effect for β-cells has previously been reported, with deleterious outcomes at low concentrations, but β-cell augmenting effects at higher concentrations (Barakat et al., 1994; Bretherton-Watt et al., 1992; Hermansen and Ahren, 1990). Our hypothesis, based on the foregoing, that in NOD mice suppressed neuropeptide secretion is a pathogenic event, was positively answered through two independent approaches: removal of TRPV1+ neurons and local i.a. pancreas injection with sP, both of which evidenced similar results.

Pancreas sP injection normalized all parameters tested: clearing of insulitis lesions, enhancement of insulin sensitivity and consequent reversal of overt diabetes that lasted for a period of weeks. This methodology is in marked contrast to the only other strategy to reverse NOD diabetes, which is toxic immunosuppression with anti-CD3 antibodies, now also in clinical trials with human diabetics (Keymeulen et al., 2005).

When viewed in their totality, our findings are inconsistent with the view that diabetes is due solely to immunological and endocrine abnormalities. Rather, our observations demonstrate that the nervous system, in particular $TRPV1^+$ primary afferent neurons, have a critical role in diabetes pathoetiology. Analogous findings in $NOD^{caps}$, NOD.Idd4 congenics and in TRPV1 knockout mice add strength to our conclusions, as does an earlier report demonstrating that another TRPV1-dependent neuropeptide, CGRP, prevents diabetes when transgenically overexpressed in the islet (Khachatryan et al., 1997).

We have recently generated preliminary evidence for insulitis and diabetes protection by selective trans-section of sensory nerves innervating the pancreas, providing yet another line of support for the role of TRPV1+ sensory neurons in T1D pathoetiology.

The mapping of several NOD disease-associated phenotypes to a single, mutant protein, TRPV1, implies that $TRPV1^+$ sensory afferents are key elements for normal islet physiology, opening broad new areas of research including insulin resistance, which remains a challenge after decades of intense investigation (LeRoith and Gavrilova, 2006), that recently has included sensory nervous system elements (Moesgaard et al., 2005).

The data generated to date has enabled us to identify the molecular mechanism that translates a system-wide genetic TRPV1 defect into pancreas-specific disease. TRPV1+ sensory neurons express high affinity insulin receptors, insulin potentiates TRPV1 currents (Van Buren et al., 2005), and lowers TRPV1 thermal activation thresholds (Sathianathan et al., 2003). At body temperature, the insulin-rich islet milieu should generate tonic TRPV1 current activation with associated neuropeptide release impacting on basal insulin secretion, a local control circuit first envisioned over a decade ago (Hermansen and Ahren, 1990). In NOD mice, this sensory nerve terminal-β-cell circuit has gone astray, with disease prevention through either its removal, or through sufficient localized supply of the deficient neuropeptide or a neuropeptide offering an equivalent mode of action.

Our data demonstrates that $TRPV1^+$ sensory afferents control pancreatic tissue access for immune cells, which may occur through modifying their immigration, residence, emigration or a combination of these elements. It is likely that progressive islet infiltration will also compound β-cell stress, which we believe is central to T1D, including attraction of autoreactive T cell pools. There is human disease precedence for a role of sensory neurons controlling lymphocyte tissue access, since rare patients without sensory nerves (CIPA syndrome) succumb to massive infections with little tissue infiltration, despite normal in vitro immune functions (Indo et al., 1996).

We discovered mutations in the coding sequence of TRPV1$^{NOD}$ gene contained within the Idd4 diabetes risk locus (Grattan et al., 2002; Ivakine et al., 2005; McAleer et al., 1995). NOD.B6.Idd4 congenic mice show normalized behavioral, electrophysiological and insulin-resistance phenotypes. Intriguingly, the TRPV1 locus is contained within other overlapping autoimmune loci (eae7, orch3, streptozotocin sensitivity) (Babaya et al., 2005; Butterfield et al., 1999; Butterfield et al., 1998), raising the possibility that TRPV1 may play a role in other autoimmune conditions. Indeed, B6 mice, relatively resistant to streptozotocin-induced T1D, show increased diabetes susceptibility in B6.TRPV1$^{-/-}$ mice (data not shown).

In conclusion, our collective findings identify TRPV1$^+$ sensory neurons as important elements of diabetes pathoetiology, with effects that are suggestive of possible mechanisms of the tissue-selectivity of the disease, its links to β-cell physiology, stress and insulin resistance. Our observations open the possibility that sensory nerve dysfunction may contribute to prediabetes initiation and progression in diabetes-prone humans.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for normalizing elevated insulin resistance and initiating resolution of islet inflammation and islet infiltration by immune cells in a mammal comprising:
delivering Substance P for ligation of neurokinin 1 receptors(NK1R receptors) by intra-arterial injection into the pancreas of said mammal wherein rapid reversal of islet inflammation, abnormal insulin resistance and diabetes occurs.

* * * * *

```
                        SEQUENCE LISTING

<160> NUMBER OF SEQ ID NOS: 24

<210> SEQ ID NO 1
<211> LENGTH: 29
<212> TYPE: PRT
<213> ORGANISM: Mus musculus

<400> SEQUENCE: 1

Thr Lys Phe Val Thr Asn Met Tyr Asn Glu Ile Leu Ile Leu Gly Ala
 1               5                  10                  15

Lys Leu His Ala Thr Leu Lys Leu Glu Glu Leu Thr Asn
            20                  25

<210> SEQ ID NO 2
<211> LENGTH: 29
<212> TYPE: PRT
<213> ORGANISM: Mus musculus

<400> SEQUENCE: 2

Thr Lys Phe Val Thr Asn Met Tyr Asn Glu Ile Leu Ile Leu Gly Ala
 1               5                  10                  15

Lys Leu His Pro Thr Leu Lys Leu Glu Glu Leu Thr Asn
            20                  25

<210> SEQ ID NO 3
<211> LENGTH: 29
<212> TYPE: PRT
<213> ORGANISM: Mus musculus

<400> SEQUENCE: 3

Thr Lys Phe Val Thr Asn Met Tyr Asn Glu Ile Leu Ile Leu Gly Ala
 1               5                  10                  15
```

Lys Leu His Pro Thr Leu Lys Leu Glu Glu Leu Thr Asn
            20                  25

<210> SEQ ID NO 4
<211> LENGTH: 29
<212> TYPE: PRT
<213> ORGANISM: Rattus sp.

<400> SEQUENCE: 4

Thr Lys Phe Val Thr Ser Met Tyr Asn Glu Ile Leu Ile Leu Gly Ala
 1               5                  10                  15

Lys Leu His Pro Thr Leu Lys Leu Glu Glu Ile Thr Asn
            20                  25

<210> SEQ ID NO 5
<211> LENGTH: 29
<212> TYPE: PRT
<213> ORGANISM: Homo sapiens

<400> SEQUENCE: 5

Thr Lys Phe Val Thr Ser Met Tyr Asn Glu Ile Leu Met Leu Gly Ala
 1               5                  10                  15

Lys Leu His Pro Thr Leu Lys Leu Glu Glu Leu Thr Asn
            20                  25

<210> SEQ ID NO 6
<211> LENGTH: 29
<212> TYPE: PRT
<213> ORGANISM: Canis sp.

<400> SEQUENCE: 6

Thr Lys Phe Val Thr Ser Met Tyr Asn Glu Ile Leu Ile Leu Gly Ala
 1               5                  10                  15

Lys Leu His Pro Thr Leu Lys Leu Glu Gly Leu Thr Asn
            20                  25

<210> SEQ ID NO 7
<211> LENGTH: 29
<212> TYPE: PRT
<213> ORGANISM: Sus sp.

<400> SEQUENCE: 7

Thr Lys Phe Val Thr Ser Met Tyr Asn Glu Ile Leu Ile Leu Gly Ala
 1               5                  10                  15

Lys Leu Tyr Pro Thr Leu Lys Leu Glu Glu Leu Thr Asn
            20                  25

<210> SEQ ID NO 8
<211> LENGTH: 29
<212> TYPE: PRT
<213> ORGANISM: Oryctolagus cuniculus

<400> SEQUENCE: 8

Thr Lys Phe Val Thr Ser Met Tyr Asn Glu Ile Leu Ile Leu Gly Ala
 1               5                  10                  15

Lys Leu His Pro Thr Leu Lys Leu Glu Glu Leu Ile Asn
            20                  25

<210> SEQ ID NO 9
<211> LENGTH: 29
<212> TYPE: PRT
<213> ORGANISM: Gallus sp.

```
<400> SEQUENCE: 9

Thr Lys Phe Val Thr Lys Met Tyr Asn Asn Ile Leu Ile Leu Gly Ala
 1               5                  10                  15

Lys Ile Asn Pro Ile Leu Lys Leu Glu Glu Leu Thr Asn
            20                  25

<210> SEQ ID NO 10
<211> LENGTH: 25
<212> TYPE: PRT
<213> ORGANISM: Mus musculus

<400> SEQUENCE: 10

Lys Leu Leu Gln Val Gly Phe Thr Pro Glu Gly Lys Asp Asp Phe Arg
 1               5                  10                  15

Trp Cys Phe Arg Val Asp Glu Val Asn
            20                  25

<210> SEQ ID NO 11
<211> LENGTH: 25
<212> TYPE: PRT
<213> ORGANISM: Mus musculus

<400> SEQUENCE: 11

Lys Leu Leu Gln Val Gly Phe Thr Pro Asp Gly Lys Asp Asp Phe Arg
 1               5                  10                  15

Trp Cys Phe Arg Val Asp Glu Val Asn
            20                  25

<210> SEQ ID NO 12
<211> LENGTH: 25
<212> TYPE: PRT
<213> ORGANISM: Mus musculus

<400> SEQUENCE: 12

Lys Leu Leu Gln Val Gly Phe Thr Pro Asp Gly Lys Asp Asp Phe Arg
 1               5                  10                  15

Trp Cys Phe Arg Val Asp Glu Val Asn
            20                  25

<210> SEQ ID NO 13
<211> LENGTH: 25
<212> TYPE: PRT
<213> ORGANISM: Rattus sp.

<400> SEQUENCE: 13

Lys Leu Leu Gln Val Gly Phe Thr Pro Asp Gly Gln Asp Asp Tyr Arg
 1               5                  10                  15

Trp Cys Phe Arg Val Asp Glu Val Asn
            20                  25

<210> SEQ ID NO 14
<211> LENGTH: 25
<212> TYPE: PRT
<213> ORGANISM: Homo sapiens

<400> SEQUENCE: 14

Lys Leu Leu Gln Val Gly Tyr Thr Pro Asp Gly Lys Asp Asp Tyr Arg
 1               5                  10                  15

Trp Cys Phe Arg Val Asp Glu Val Asn
            20                  25
```

```
<210> SEQ ID NO 15
<211> LENGTH: 25
<212> TYPE: PRT
<213> ORGANISM: Canis sp.

<400> SEQUENCE: 15

Lys Leu Leu Gln Val Gly Tyr Thr Pro Asp Gly Lys Asp Asp Tyr Arg
 1               5                  10                  15

Trp Cys Phe Arg Val Asp Glu Val Asn
            20                  25

<210> SEQ ID NO 16
<211> LENGTH: 25
<212> TYPE: PRT
<213> ORGANISM: Sus sp.

<400> SEQUENCE: 16

Lys Leu Leu Gln Val Gly Phe Thr Pro Asp Gly Gln Asp Asp Tyr Arg
 1               5                  10                  15

Trp Cys Phe Arg Val Asp Glu Val Asn
            20                  25

<210> SEQ ID NO 17
<211> LENGTH: 25
<212> TYPE: PRT
<213> ORGANISM: Oryctolagus cuniculus

<400> SEQUENCE: 17

Lys Leu Leu Gln Val Gly Tyr Thr Pro Asp Gly Lys Asp Asp Tyr Arg
 1               5                  10                  15

Trp Cys Phe Arg Val Asp Glu Val Asn
            20                  25

<210> SEQ ID NO 18
<211> LENGTH: 25
<212> TYPE: PRT
<213> ORGANISM: Gallus sp.

<400> SEQUENCE: 18

Lys Arg Val Leu Val Gly Ile Thr Pro Asp Gly Gln Asp Asp Tyr Arg
 1               5                  10                  15

Trp Cys Phe Arg Val Asp Glu Val Asn
            20                  25

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atggagaaat gggctagctt ag                                          22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
```

```
tcatttctcc cctggggcca tgg                                            23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgttgtcagc tgtgttatct gcc                                            23

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttcagccatc gcaaggagta                                                20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggagaaatgg gctagcttag                                                20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaagacctca gcatcctctg g                                              21
```